(12) United States Patent
Rohr et al.

(10) Patent No.: US 9,447,135 B2
(45) Date of Patent: Sep. 20, 2016

(54) SEMI-SYNTHETIC MITHRAMYCIN DERIVATIVES WITH ANTI-CANCER ACTIVITY

(71) Applicant: UNIVERSITY OF KENTUCKY RESEARCH FOUNDATION, Lexington, KY (US)

(72) Inventors: Jurgen T. Rohr, Lexington, KY (US); Daniel Scott, Greencastle, IN (US); Markos Leggas, Lexington, KY (US); Jhong-Min Chen, Lexington, KY (US); Oleg V. Tsodikov, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 14/717,542

(22) Filed: May 20, 2015

(65) Prior Publication Data

US 2016/0024130 A1    Jan. 28, 2016

Related U.S. Application Data

(63) Continuation of application No. PCT/US2013/074725, filed on Dec. 12, 2013.

(60) Provisional application No. 61/737,353, filed on Dec. 14, 2012, provisional application No. 62/001,516, filed on May 21, 2014.

(51) Int. Cl.

| | |
|---|---|
| *A01N 43/04* | (2006.01) |
| *A61K 31/70* | (2006.01) |
| *C07H 15/24* | (2006.01) |
| *C07H 1/00* | (2006.01) |
| *A61K 31/704* | (2006.01) |
| *A61K 31/7034* | (2006.01) |

(52) U.S. Cl.
CPC ............... *C07H 15/24* (2013.01); *C07H 1/00* (2013.01); *A61K 31/704* (2013.01); *A61K 31/7034* (2013.01)

(58) Field of Classification Search
None
See application file for complete search history.

(56) References Cited

U.S. PATENT DOCUMENTS

| | | | |
|---|---|---|---|
| 5,976,813 A | 11/1999 | Beutel et al. | |
| 6,472,144 B2 | 10/2002 | Malin et al. | |
| 6,692,856 B2 | 2/2004 | Smotkin | |
| 6,824,982 B1 | 11/2004 | Reetz et al. | |
| 7,423,008 B2 | 9/2008 | Rohr et al. | |
| 2012/0270823 A1 | 10/2012 | Nunez Gonzaez et al. | |
| 2013/0101632 A1 | 4/2013 | Scott et al. | |

FOREIGN PATENT DOCUMENTS

GB    1446536 A    8/1976

OTHER PUBLICATIONS

Barcelo et al. Biochemistry (2010), vol. 49, pp. 10543-10552.*
International Search Report PCT/US2013/074725 dated Apr. 15, 2014.
Youcai Hu et al., "Chromomycin SA analogs from a marine-derived *Streptomyces* sp.", Bioorg. Med. Chem., Sep. 1, 2011, 19(17), pp. 5183-5189.

* cited by examiner

*Primary Examiner* — Patrick Lewis
(74) *Attorney, Agent, or Firm* — McDermott Will & Emery LLP

(57) ABSTRACT

Mithramycin derivatives and their pharmaceutically acceptable salts are disclosed. The mithramycin derivatives can be used in the treatment of Ewing sarcoma or other cancer or neuro-disease associated with an aberrant erythroblast transformation-specific transcription factor.

16 Claims, 12 Drawing Sheets

(SEQ ID NO:07)

```
  1  mdgtikeals vvsddqslfd saygaaahlp kadmtasgsp dygqphkinp lppqqewinq
 61  pvrvnvkrey dhmngsresp vdcsvskcsk lvgggesnpm nynsymdekn gppppnmttn
121  errvivpadp tlwtqehvrq wlewaikeys lmeidtsffq nmdgkelckm nkedflratt
181  lyntevllsh lsylressll aynttshtdq ssrlsvkedp sydsvrrgaw gnnmnsglnk
241  spplggaqti sknteqrpqp dpyqilgpts srlanpgsgq iqlwqfllel lsdsanasci
301  twegtngefk mtdpdevarr wgerkskpnm nydklsralr yyydknimtk vhgkryaykf
361  dfhgiaqalq phptessmyk ypsdisymps yhahqqkvnf vpphpssmpv tsssffgaas
421  qywtsptggi ypnpnvprhp nthvpshlgs yy
```

FIG. 6

(SEQ ID NO:08)

```
  1  miqtvpdpaa hikealsvvs edqslfecay gtphlaktem tassssdygq tskmsprvpq
 61  qdwlsqppar vtikmecnps qvngsrnspd ecsvakggkm vgspdtvgmn ygsymeekhm
121  pppnmttner rvivpadptl wstdhvrqwl ewavkeyglp dvnillfqni dgkelckmtk
181  ddfqrltpsy nadillshlh ylretplphl tsddvdkalq nsprlmharn tdlpyepprr
241  sawtghghpt pqskaaqpsp stvpktedqr pqldpyqilg ptssrlanpg sgqiqlwqfl
301  lellsdssns scitwegtng efkmtdpdev arrwgerksk pnmnydklsr alryyydkni
361  mtkvhgkrya ykfdfhgiaq alqphppess lykypsdlpy mgsyhahpqk mnfvaphppa
421  lpvtsssffa apnpywnspt ggiypntrlp tshmpshlgt yy
```

FIG. 7

SEQ ID NO:01 : 1 pgsgqiqlwq fllellsdsa nascitwegt ngefkmtdpd evarrwgerk
                 skpnmnydkl sralryyydk nimtkvhgkr yaykfdfhgi aqalqphp 98

SEQ ID NO:02  1 pgsgqiqlwq fllellsdss nsscitwegt ngefkmtdpd evarrwgerk skpnmnydkl
                sralryyydk nimtkvhgkr yaykfdfhgi aqalqphp 98

FIG. 8

SEMI-SYNTHETIC MITHRAMYCIN DERIVATIVES WITH ANTI-CANCER ACTIVITY

CROSS-REFERENCE TO RELATED APPLICATIONS

This application is a continuation application of PCT/US2013/074725, filed Dec. 12, 2013, which claims the benefit of U.S. Provisional Application No. 61/737,353 filed Dec. 14, 2012, and this application claims the benefit of U.S. Provisional Application No. 62/001,516, filed May 21, 2014. The entire disclosures of the foregoing PCT and Provisional Patent Applications are hereby incorporated by reference herein.

SEQUENCE LISTING

The instant application contains a Sequence Listing which has been submitted electronically in ASCII format and is hereby incorporated by reference in its entirety. Said ASCII copy, created on Jul. 23, 2015, is named 050229-0635_SL.txt and is 12,125 bytes in size.

TECHNICAL FIELD

The present disclosure relates to mithramycin side chain carboxylic acid (MTM SA) derivatives and their use in the treatment of cancers. The present disclosure also relates to methods for identifying MTM SA derivative compounds that selectively modulate the activity of a target ETS transcription factor.

BACKGROUND

All members of the erythroblast transformation-specific (ETS) transcription factor-family contain an Ets-domain which consists of approximately 80 amino acids with four tryptophan repeats. The Ets-domain binds to double-stranded DNA of target genes containing a GGAA/T core motif and different flanking regions. Exemplary ETS transcription factors include Friend leukemia integration 1 transcription factor (FLI1) and v-ets avian erythroblastosis virus E26 oncogene-like transcription factor (ERG).

FLI1 aberrant regulation is often associated with malignant transformation and is associated with chromosomal abnormalities in humans. For example, in Ewing Sarcoma and primitive neuroectodermal tumors, a chromosomal translocation results in a chimeric EWS-FLI1 fusion protein, containing the 5' region of EWS (Ewing sarcoma breakpoint region 1) and the 3' ETS region of Fli-1 (Delattre et al., Nature. 1992 Sep. 10; 359(6391):162-5). This oncoprotein acts as an aberrant transcriptional activator with strong transforming capabilities. FLI1 and homologous transcription factors also have been implicated in human leukemias, such as Acute Myelogenous Leukemia (AML), involving loss or fusion of the tel gene, as well as other malignancies including clear-cell sarcoma, myxoid liposarcoma, desmoplastic small round cell tumor, myxoid chondrosarcoma, acute myeloid leukemia, congenital fibrosarcoma, prostate cancer and pancreatic cancer.

Another ETS transcription factor, ERG, is implicated in several cancers. Aberrant ERG regulation has been shown to be associated with diseases including Ewing sarcoma, acute myeloid leukemia (AML), prostate cancer, acute lymphoblatic leukemia (ALL), Alzheimer's disease (AD), and Down syndrome (DS).

Although ETS transcription factors such as FLI1 and ERG have been identified as critical targets in diseases such as Ewing sarcoma, no therapies have yet moved from bench to bedside that could impact the outcome of this disease. Ewing sarcoma, which affects primarily children and young adults is a difficult cancer to treat. Current therapy with a combination of severely cytotoxic drugs provides up to 60% long-term survival, but the cancer often recurs.

Recently, mithramycin (MTM), an aureolic acid natural product previously used clinically against other cancers, was identified as a potent (low-nM) inhibitor of EWS-FLI1 in Ewing sarcoma cells (Grohar et al., (2011) *Journal of the National Cancer Institute* 103, 962-78). MTM exhibited similar high potency against Ewing sarcoma tumor cells in vitro and was efficacious in Ewing sarcoma mouse xenografts. Based on this study, MTM entered clinical trials at the National Cancer Institute as a Ewing sarcoma therapeutic (ClinicalTrials.gov, ID#NCT01610570) in 2012. Despite its strong inhibitory properties towards Ewing sarcoma, MTM was found to be highly toxic to non-Ewing cells, apparently because it inhibits Sp transcription factors. Therefore, MTM analogues that are more selective against Ewing sarcoma cells and/or other cancers are needed.

It is clear that MTM has high potential in the fight against cancer and new and improved analogues would find clinical relevance. A need thus exists to improve the performance, selectivity and efficacy of MTM.

SUMMARY OF THE DISCLOSURE

In one aspect of the disclosure, certain MTM SA derivatives or their pharmaceutically acceptable salts are provided. Such derivatives can be used in the treatment of various cancers including Ewing sarcoma and various neuro-diseases. In certain embodiments there are provided MTM SA derivatives having the following formula:

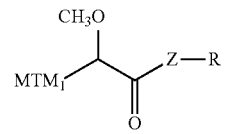

or a pharmaceutically acceptable salt thereof; wherein Z represents O, S, N—R'; R and R' represent, for each occurrence, H, alkyl, heterocyclic, aryl, heteroaryl, provided that R is not H when Z is O; ZR taken together represents an organic residue, e.g., an amino acid conjugate or its ester derivative; and wherein $MTM_1$ represents the fused ring portion of the mithramycin structure and can include different sugars or sugar chains.

In certain embodiments, the MTM SA derivative is an amide derivative, e.g. ZR together form a $NR_1R_2$ group where $R_1$ and $R_2$ can be the same or different and each of $R_1$ and $R_2$ can be an H, an amino acid conjugate or an ester derivative thereof, a lower straight chain or branched alkyl. In other embodiments, the MTM SA derivative is an amino acid derivative, e.g. $NR_1R_2$ together form an amino acid conjugate or an ester derivative thereof. In certain embodiments, $NR_1R_2$ is the amino acid conjugate phenylalanine (e.g., MTM SA-Phe) or an ester derivative thereof. In other embodiments, $NR_1R_2$ is the amino acid conjugate tryptophan (e.g., MTM SA-Trp) or its ester derivative. The amino acid conjugate or its ester derivative thereof can further be substituted. Substituents include, for example, —$R_3Y$ where $R_3$ is alkyl, e.g., $C_{1-16}$ or $C_{1-8}$ alkyl, and Y is a formyl ene, expoxy, aryl, e.g., phenyl, heteroaryl, e.g., indolyl. In some embodiments —$R_3Y$ together form an allylox group. In another related embodiment, the MTM SA derivative includes one or more sugar groups such as D-digitoxose. In another related embodiment, the MTM SA derivative is MTM SA-Phe or MTM SA-Trp that also includes one or more different sugar moieties.

In another aspect, the subject technology provides a method for screening MTM SA derivatives to identify derivatives that selectively complex with and specifically modulate the activity of a target ETS transcription factor that has a DNA binding domain with an amino acid sequence that is at least 85% identical to SEQ ID NO:01 or SEQ ID NO:02 over the entire length of either of these sequences. In a related embodiment, the screening method includes use of an isolated mutant ETS transcription factor described herein. In another related embodiment, the screening method includes the step of (a) contacting a mithramycin derivative as a test agent or a test agent other than mithramycin with a target ETS transcription factor in the presence of an oligonucleotide substrate under conditions suitable for transcription of the oligonucleotide substrate; (b) detecting the specificity of the test agent for binding to and/or modulating the activity of the target ETS transcription factor, and (c) selecting test agents that exhibit specifically for and modulate the activity of the target ETS transcription factor relative to a reference or control sample or one or more other ETS transcription factors. In another embodiment, the screening method includes the steps of (a) contacting a mithramycin derivative as a test agent or a test agent other than mithramycin with the target ETS transcription factor in the presence of an oligonucleotide substrate; (b) assessing the effect of the test agent on the activity of the target ETS transcription factor; and (c) selecting test agents that exhibit specificity for and modulate the activity of the ETS transcription factor relative to a reference or control sample or one or more other ETS transcription factors.

In another embodiment relating to this aspect, the target ETS transcription factor is Friend leukemia integration 1 transcription factor (FLI1) or v-ets avian erythroblastosis virus E26 oncogene-like transcription factor (ERG). In another related embodiment relating to this aspect, the specificity of the test agent for the target ETS transcription is assessed by detecting the formation and/or stability of a complex formed between the transcription factor and its oligonucleotide substrate in the presence of the test agent relative to a reference or control sample or one or more other ETS transcription factors. In another related embodiment, the effect of the test agent on the activity the transcription factor is assessed by detecting the formation and/or stability of a complex formed between the transcription factor and the oligonucleotide substrate in the presence of the test agent relative to a reference or control sample. In another related embodiment, the activity of the test agent is assessed by measuring the effect of the test compound on the affinity of the transcription factor for the oligonucleotide substrate. In another related embodiment, step (b) discussed above further includes assessing the formation of a complex comprising the MTM SA derivative, the target ETS transcription factor and the oligonucleotide substrate.

In another aspect, the subject technology provides a method for modulating the activity of a target erythroblast transformation-specific (ETS) transcription factor in a patient in need thereof, including administering to the patient a therapeutically effective amount of an MTM SA derivative or a pharmaceutically acceptable salt thereof having the following formula:

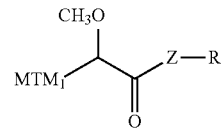

or a pharmaceutically acceptable salt thereof; wherein Z and R represent the same groups as described herein, including all of the various embodiments thereof.

In another aspect, the subject technology provides a method of treating a target ETS transcription factor-mediated disease in a patient by administering to the patient a therapeutically effective amount of an MTM SA-Phe, MTM SA-Trp or any other MTM SA derivative described herein, wherein the MTM SA derivative specifically modulates the activity of the ETS transcription factor mediating the disease and wherein the target ETS-mediated disease is Ewing sarcoma, clear-cell sarcoma, myxoid liposarcoma, desmoplastic small round cell tumor, myxoid chondrosarcoma, acute myeloid leukemia, congenital fibrosarcoma, prostate cancer or pancreatic cancer. In an embodiment of this aspect, the target ETS transcription factor specifically modulated is Friend leukemia integration 1 transcription factor (FLI1) or v-ets avian erythroblastosis virus E26 oncogene-like transcription factor (ERG).

In another aspect, the subject technology provides an isolated non-naturally-occurring mutant or engineered ETS transcription factor that comprises a DNA binding domain having the sequences of SEQ ID NO:01 or SEQ ID NO:02, wherein the transcription factor includes at least one amino acid substitution at any of amino acid residues corresponding to residues Tyr68, Lys75, His77, Gly78, Lys79, Arg80, Tyr81, Ala82 of SEQ ID NO:01 or SEQ ID NO:02. In an embodiment relating to this aspect, the engineered ETS transcription factor comprises a DNA binding domain that is at least 85% identical to SEQ ID NO:01 or SEQ ID NO:02 over the entire length of either of these sequences. In another related embodiment the engineered ETS transcription factor is Friend leukemia integration 1 transcription factor (FLI1) or v-ets avian erythroblastosis virus E26 oncogene-like transcription factor (ERG). In another related embodiment, the engineered ETS transcription factor has a substantially similar, increased, or decreased DNA binding activity relative to the DNA binding activity of a wild-type ETS transcription factor.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 6 shows the amino acid sequence (SEQ ID NO: 7) of FLI1 transcription factor, with the DNA binding domain in that sequence highlighted.

FIG. 7 shows the amino acid sequence (SEQ ID NO: 8) of ERG transcription factor, with the DNA binding domain in that sequence highlighted.

FIG. 8 shows a comparison between the amino acid sequences of the DNA binding domains of FLI1 (SEQ ID NO:01) and ERG (SEQ ID NO:02), with the MTM interacting residues underlined.

DETAILED DESCRIPTION OF THE DISCLOSURE

Figure 1:
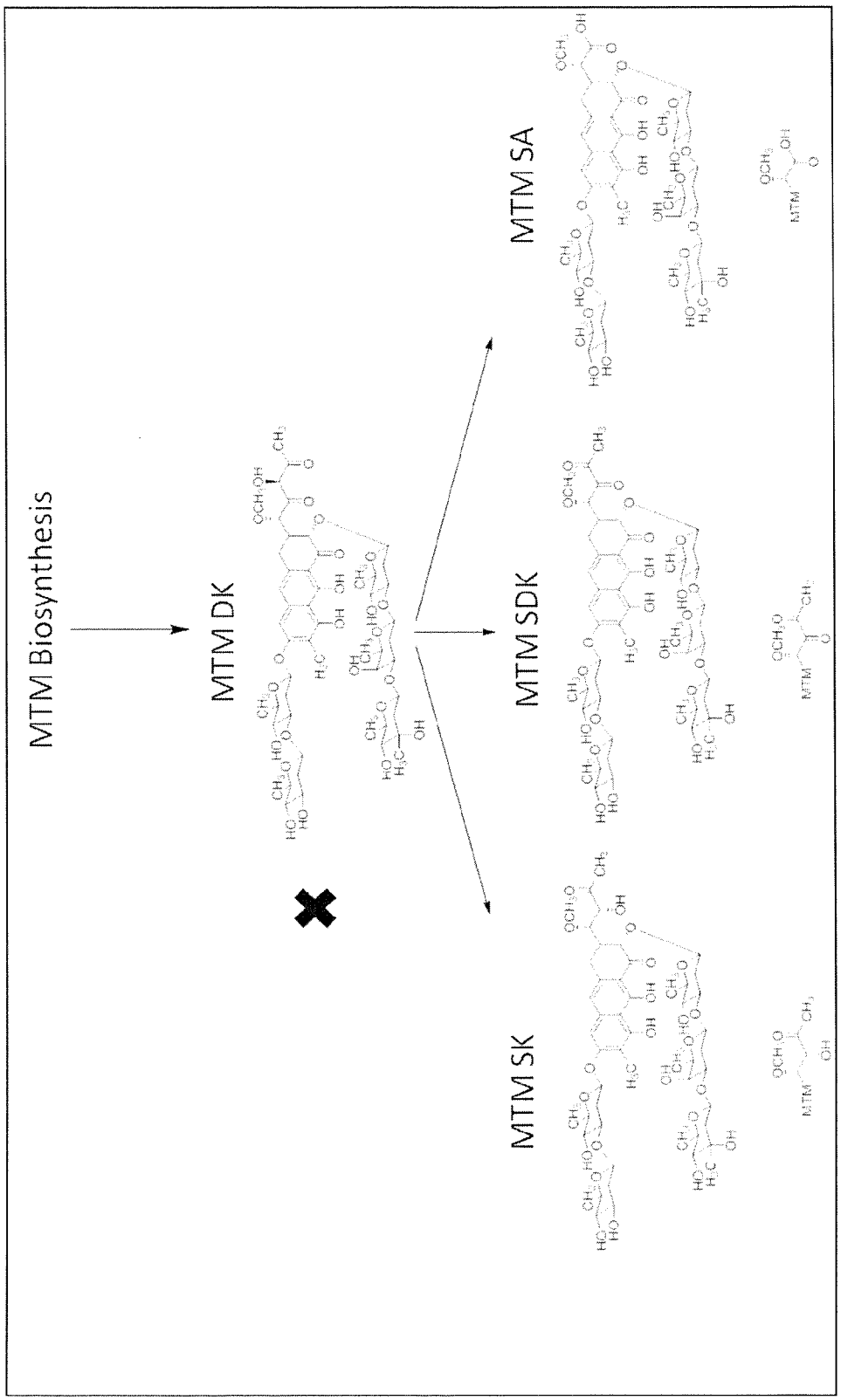
FIG. 1 is a schematic representation of the accumulation of MTM SK, MTM SDK, and MTM SA by the inactivation of the mtmW gene in the MTM biosynthetic pathway.

The MTM SA derivatives disclosed herein are examples of modified natural products that exhibit improved anticanceractivity in comparision to the natural product. It is believed that MTM acts by cross-linking GC-rich DNA thereby shutting down the transcription of several proto-oncogenes, particularly pathways regulated by transcription factors Sp1 and Sp3. The Sp1 transcription factors are important as they have been linked to the control of cell growth, survival, and differentiation and their overexpression has been observed in several cancers.

Extensive combinatorial biosynthesis has been performed on the drug biosynthesis pathway to produce altered MTM analogues for the purpose of improving their toxicity profiles. This has resulted in several novel useful compounds for the treatment of Ewing sarcoma and other cancers.

The inventors have discovered inter alia that MTM SA binds DNA substrate together and cooperatively with EWS-FLI1, resulting in a ternary MTM SA:DNA substrate:EWS-FLI1 complex, which, in turn, perturbs the transcription function of EWS-FLI1 required for oncogenesis and tumor progression. The inventors have identified certain MTM SA derivatives including MTM SA-Phe and MTM SA-Trp that exhibit greater selectivity for EWS-FLI1 transcription factor and against Ewing's sarcoma cells than MTM itself.

The systematic investigations of the DNA interaction of certain of these lead drugs led to discovery of the mechanism of action of MTM, which not only explains all effects of MTM observed thus far, but now serves as the basis for further systematic improvement and fine-tuning of the lead analogues. Briefly, the inventors have found that MTM increases the binding affinity of EWS-FLI1 to promoter DNA both by DNA remodeling and through specific direct MTM-EWS-FLI1 interactions, i.e., locks a ternary drug-DNA-transcription factor complex. This mechanism is fundamentally different from the generally accepted mechanism of action of MTM (displacement of Sp-type transcription factors from the DNA promoter region by MTM), which can account for the general toxicity of MTM, but cannot explain its potent and selective antagonism of EWS-FLI1. The discovery of a direct interaction between MTM, bound in the minor groove of the DNA, and the transcription factor EWS-FLI1, bound in the nearby major groove, was utilized to generate optimized MTM analogues with increased specificity for a target transcription factor.

In the following detailed description, numerous specific details are set forth to provide a full understanding of the subject technology. It will be apparent, however, to one of ordinarily skilled in the art that the subject technology may be practiced without some of these specific details. In other instances, well-known structures and techniques have not been shown in detail so as not to obscure the subject technology.

All references cited herein are incorporated by reference in their entirety as though fully set forth. Unless defined otherwise, technical and scientific terms used herein have the same meaning as commonly understood by one of ordinary skill in the art to which subject technology belongs.

DEFINITIONS

To facilitate an understanding of the present subject technology, a number of terms and phrases are defined below:

A reference to an element in the singular is not intended to mean "one and only one" unless specifically stated, but rather "one or more."

As used herein, a "target ETS transcription factor" refers to a transcription factor which comprises a DNA-binding domain (DBD) having an amino acid sequence that is at least 85% identical to SEQ ID NO:01 or SEQ ID NO:02 over the entire length of either of these sequences. SEQ ID NO:01 and SEQ ID NO:02 are provided in FIG. 8.

As used herein the term "modulator," "modulating," or "modulate" in connection with the target ETS transcription factor of the subject technology refers to any agent that has a functional effect on the transcription factor, including positively or negatively affecting its binding to a DNA substrate, positively or negatively affecting the formation and/or stability of a complex formed between the transcription factor and its oligonucleotide substrate, positively or negatively affecting its function in causing the transcription of its oligonucleotide substrate.

As used herein, the term "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "variant" in relation to the amino acid sequence of the ETS transcription factors refers to a naturally occurring allelic variant of the ETS transcription factors such as those shown in SEQ ID NO:07 and SEQ ID NO:08, which includes any substitution of, variation of, modification of, replacement of, deletion of or addition of one (or more) amino acids provided the resultant ETS transcription factor has a transcription factor activity and has a DNA binding domain that is at least 85% identical to SEQ ID NO:01 or SEQ ID NO:02 over the entire length of either of these sequences. For example, a variant of ETS transcription factor may have at least 50%, or at least 60%, or at least 70% sequence identity with the ETS transcription factors such as those shown in SEQ ID NO:07 and SEQ ID NO:08 over the entire length of the sequence, provided that the variant has a transcription factor activity and has a DNA binding domain that is at least 85%, at least 90%, at least 95% or at least 98% identical to SEQ ID NO:01 or SEQ ID NO:02 over the entire length of either of these sequences.

The terms "percentage of sequence identity" or "percentage homology" and any equivalent terms are used interchangeably herein to refer to comparisons among polynucleotides and polypeptides, and are determined by comparing two optimally aligned sequences over a comparison window, wherein the portion of the oligonucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB [Pearson and Lipman, (1988), Proc. Natl. Acad. Sci. USA 85(8): 2444-2448; Altschul et al., (1990), J. Mol. Biol. 215(3):403-410; Thompson et al. (1994), Nucleic Acids. Res. 22(2): 4673-4680; Higgins et al., (1996), Meth. Enzymol. 266:383-402; Altschul et al., (1993), Nature Genetics 3:266-272; Brutlag et al. (1990) Comp. App. Biosci. 6:237-24], the disclosures of which are incorporated by reference in their entireties. In an embodiment, protein and nucleic acid sequence identities are evaluated using the Basic Local Alignment Search Tool ("BLAST") which is well known in the art [e.g., Karlin and Altschul, (1990), Proc. Natl. Acad. Sci. USA 87:2267-2268; Altschul et al., (1997), Nuc. Acids Res. 25:3389-3402] the disclosures of which are incorporated by reference in their entireties.

As used herein, an "oligonucleotide substrate" in reference to a substrate of a target ETS transcription factor refers to an oligonucleotide which comprises a target ETS transcription factor binding site. An oligonucleotide substrate can be single-stranded, double-stranded, or a hairpin. Preferably, an oligonucleotide substrate is double stranded. An oligonucleotide substrate can be DNA, RNA or a chimeric (comprising both deoxy and ribose nucleotides) or comprise one or more oligonucleotide modifications described herein.

As used herein, the term "transcription factor binding site" refers to a nucleic acid sequence that is recognized and bound by a transcription factor and mediates the transactivation of a reporter gene in response to that binding. Without limitations, a transcription binding site can be from any of various species including human, mouse, rat, guinea pig and the like. In some embodiments, the transcription factor binding site is a target ETS binding site such as a FLI1 binding site or an ERG binding site.

The MTM SA derivatives of the subject technology can be synthesized according to the methods described below.

The inactivation of the mtmW gene, which is the gene encoding the last acting enzyme in the MTM biosynthetic pathway, produced MTM analogues with a short side chain ketone (SK) and MTM with a short side chain diketone (SDK) (FIG. 1). Both of these analogues possess shorter side chains at the 3-position. The 3-side chain has been identified previously as important, since it is in part responsible for MTM's interaction with the DNA phosphate backbone. See U.S. Pat. No. 7,423,008. Both MTM SK and MTM SDK showed increased activity against several cancer cell lines compared to the parent MTM. These results indicate that the 3-side chain is important for the activity of MTM and offers a base for further molecular manipulations. As an unwanted side product along with the production of the desired MTM SK and MTM SDK analogues, MTM side chain carboxylic acid (SA) is also accumulated in the MtmW-minus-mutant, but showed in contrast to MTM SK and MTM SDK significantly decreased activity compared to MTM.

MTA SA is shown in formula (I) below:

(I)

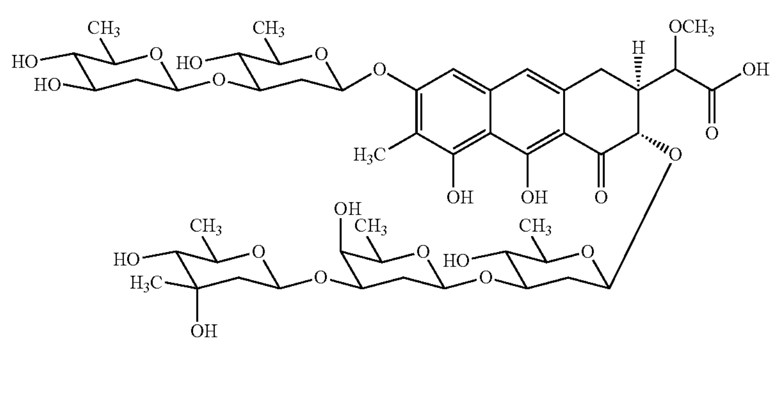

One reason for MTM-SA's decreased activity might be that its 3-side chain is too short and its negatively charged carboxylic acid does not sufficiently interact with naturally negatively charged DNA. To overcome these potential deficiencies, a semi-synthetic approach was used herein to chemically modify the unique carboxylic acid moiety of MTM SA to introduce new functionalities into the 3-side chain. In one aspect of the present disclosure, the MTM SA derivatives have the following formula:

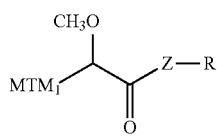

II where Z represents O, S, N—R'; R and R' represent, for each occurrence, H, alkyl, e.g., lower straight chain or branched alkyl, heterocyclic, aryl, e.g., phenyl, naphthyl, heteroaryl, e.g., pyridyl, pyrolidyl, piperidyl, pyrimidyl, indolyl, thienyl, provided that R is not H when Z is O; ZR taken together represents an organic residue, e.g., an alkyl, e.g., lower straight chain or branched alkyl, heterocyclic, aryl, e.g., phenyl, naphthyl, heteroaryl, e.g., pyridyl, pyrolidyl, piperidyl, pyrimidyl, indolyl, thienyl, an amino acid conjugate or its ester derivative, e.g., proline (Pro), alanine (Ala), serine (Ser), cysteine (Cys), histidine (His), tryptophan (Trp), tyrosine (Tyr), phenylalanine (Phe) conjugate, etc., a sugar or sugar chain. Each of the alkyl, heterocyclic, aryl, heteroaryl, sugar, or sugar chain of R, R' and ZR can be unsubstituted or substituted with one or more amino, alkyl amino, alkylcarboxyl, alkoxyl, alkylcarbonyl, hydroxyl, thio, alkyldisulfide, heterocyclic, aryl, heteroaryl, halo, e.g., fluoro, chloro, bromo, iodo, an amino acid conjugate, ether, ester, amide residue, etc. The group $MTM_1$ represents the fused ring portion of the mithramycin structure and can include different sugars or sugar chains. In other words, $MTM_1$ represents the structure of formula III below, but also variants with different sugar patterns.

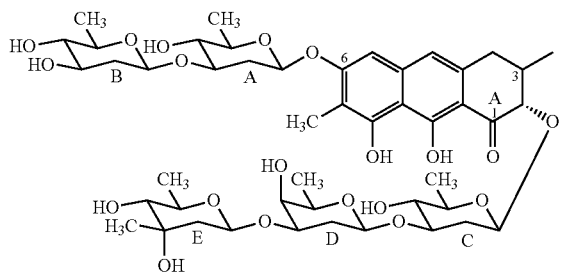

III

Thus, the A, B, C, D, E, sugars can be different from those shown, and include chain variants. Such sugars are disclosed, for example, in: (a) Baig, I.; Pérez, M.; Braña, A. F.; Gomathinayagam, R.; Damodaran, C.; Salas, J. A.; Méndez, C.; Rohr, J., Mithramycin analogues generated by combinatorial biosynthesis show improved bioactivity. *J. Nat. Prod.* 2008, 71 (2), 199-207; (b) Pérez, M.; Baig, I.; Braña, A. F.; Salas, J. A.; Rohr, J.; Méndez, C., Generation of new derivatives of the antitumor antibiotic mithramycin by altering the glycosylation pattern through combinatorial biosynthesis. *ChemBioChem* 2008, 9 (14), 2295-2304; (c) Nuñez, L. E.; Nybo, S. E.; Gonzalez-Sabin, J.; Pérez, M.; Ménendez, N.; Braña, A. F.; He, M.; Morís, F.; Salas, J. A.; Rohr, J.; Méndez, C., A Novel Mithramycin Analogue with High Antitumor Activity and Less Toxicity Generated by Combinatorial Biosynthesis. *J. Med. Chem.* 2012, 55, 5813-5825; (d) Remsing, L. L.; Garcia-Bernardo, J.; Gonzalez, A. M.; Künzel, E.; Rix, U.; Braña, A. F.; Bearden, D. W.; Méndez, C.; Salas, J. A.; Rohr, J., Ketopremithramycins and ketomithramycins, four new aureolic acid-type compounds obtained upon inactivation of two genes involved in the biosynthesis of the deoxysugar moieties of the antitumor drug mithramycin by *Streptomyces argillaceus*, reveal novel insights into post-PKS tailoring steps of the mithramycin biosynthetic pathway. *J. Am. Chem. Soc.* 2002, 124 (8), 1606-1614; (e) Remsing, L. L.; Bahadori, H. R.; Carbone, G. M.; McGuffie, E. M.; Catapano, C. V.; Rohr, J., Inhibition of c-src transcription by mithramycin: structure-activity relationships of biosynthetically produced mithramycin analogues using the c-src promoter as target. *Biochemistry* 2003, 42 (27), 8313-8324. Pharmaceutically acceptable salts of the MTM SA derivative are also contemplated by the present disclosure.

Preferably, Z represents NH, O, or S and R represents alkyl, aryl, heterocyclic, heteroaryl, etc., and when ZR is taken together, ZR represents an amino acid conjugate or its ester (e.g., a methyl ester). In certain embodiments, the MTM SA derivative is an amide derivative, e.g. ZR together form a $NR_1R_2$ group where $R_1$ and $R_2$ can be the same or different and each of $R_1$ and $R_2$ can be an H, alkyl, or an amino acid conjugate or an ester derivative thereof. In other embodiments, the MTM SA derivative is an amino acid derivative, e.g. $NR_1R_2$ together form an amino acid conjugate or an ester derivative thereof which can be further substituted.

Previous work by Preobrazhenskaya et al. (References numbered 26-28) on olivomycin derivatizations showed that introduction of N-atoms can improve aureolic acid type anticancer drugs. The inventors discovered that MTM SA derivatives with N-atoms can have improved efficacy. In one embodiment of the present disclosure, MTM SA is derivatized with an amine to form an amide. Such MTM SA amide derivatives advantageously have an elongated 3-side chain and one or more N-atom/s, which can enhance the interaction of the derivative with the DNA-phosphate backbone resulting in improved efficacy. In one aspect of the present disclosure, the MTM SA derivative is provided by formula (IV) below:

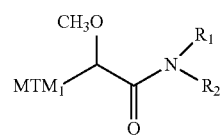

IV where $R_1$ and $R_2$ can be the same or different and each of $R_1$ and $R_2$ can be an H, an amino acid conjugate or ester thereof, a lower straight chain or branched alkyl unsubstituted or substituted with one or more amino, alkyl amino, alkylcarboxyl, alkoxyl, alkylcarbonyl, hydroxyl, thio, alkyldisulfide, halo, e.g., fluoro, chloro, bromo, iodo, provided that $R_1$ and $R_2$ are not both H simultaneously. The amino acid conjugate and ester derivatives that can be included in formula (V), e.g., where $NR_1R_2$ form an amino acid conjugate or ester derivative thereof, include, for example, a proline (Pro, or O-alkyl-Pro), alanine (Ala, or O-alkyl-Ala), serine (Ser, or O-alkyl-Ser), cysteine (Cys, or O-alkyl-Cys), histidine (His, or O-alkyl-His), tryptophan (Trp, or O-alkyl-Trp), tyrosine (Tyr, or O-alkyl-Tyr), and phenylalanine (Phe, or O-alkyl-Phe) conjugate. Further, the amino acid conjugate or its derivative can be substituted, e.g., substituted with —$R_3Y$ where $R_3$ is alkyl, e.g., $C_{1-16}$ or $C_{1-8}$ alkyl, and Y is a formyl, ene, expoxy, aryl, e.g., phenyl, heteroaryl, e.g., indolyl, group. In some embodiments —$R_3Y$ together form an allylox group. In some embodiments, the amino acid conjugate is phenylalanine (e.g., MTM SA-Phe) or an ester derivative thereof or tryptophan (e.g., MTM SA-Trp) or its ester derivative. Each of the MTM SA-Trp and MTM SA-Phe and its ester derivatives can further be substituted, e.g., substituted with —$R_3Y$.

In one embodiment of the present disclosure, the MTM SA derivative is an amino acid derivative, i.e., at least one of $R_1$ or $R_2$ is an amino acid conjugate, e.g., proline (Pro), alanine (Ala), serine (Ser), cysteine (Cys), histidine (His), tryptophan (Trp), tyrosine (Tyr), conjugate. Preferably $R_1$ is an amino acid conjugate and $R_2$ is H. For example, the MTM SA derivative can be a MTM SA 0-Me-tryptophan derivative as shown in formula V below:

also neuroprotective and the MTM SA derivative can be used to treat various neuro-diseases, such as Huntington disease, etc.

The biosynthesis of MTM SK and MTM SDK is accomplished through a genetically engineered S. argillaceus strain, M7W1, which contains an inactivated mtmW gene coding for the MtmW enzyme. Both the MTM SK and MTM SDK analogues have improved activity compared to the parent MTM compound, thus it would be optimal if these were the only two compounds produced by the M7W1 strain. However, this is not the case, and two other major compounds are produced alongside of MTM SK and MTM SDK. One of these compounds, MTM SA, has previously been disregarded as invaluable due to the relative lack of biological activity compared to the parent compound. This is unfortunate as MTM SA is produced in many fermentations in higher amounts than MTM SK or MTM SDK, and the production yield can be shifted even further in favor of the production of MTM SA by altering the pH of the culture media. Since MTM SK and MTM SDK are separated chromatographically MTM SA is easily collected and isolated alongside MTM SK and MTM SDK during the normal isolation procedure.

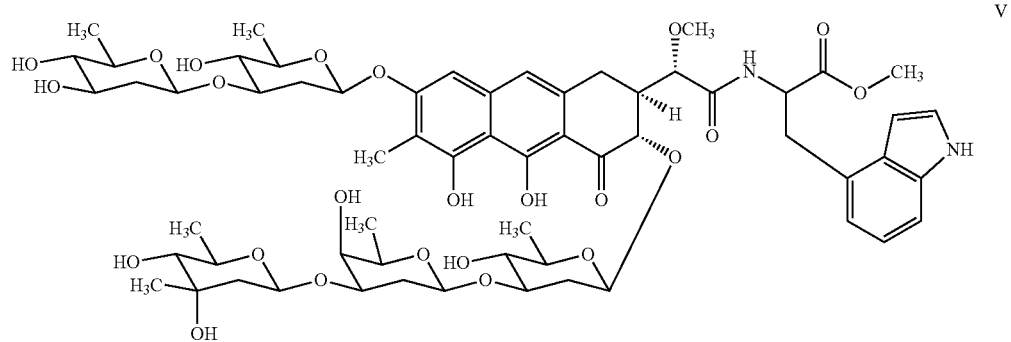

V

Figure 2:
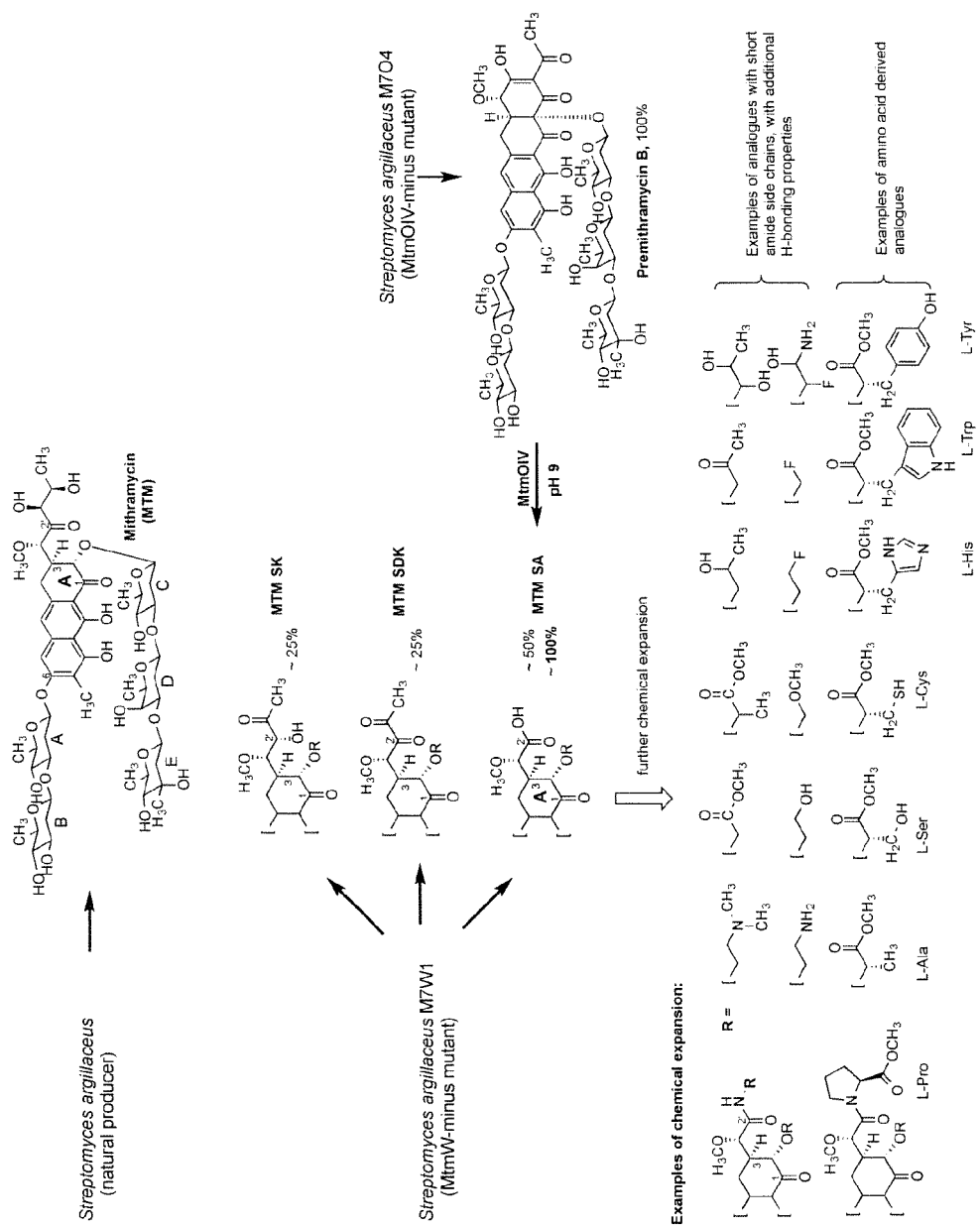
FIG. 2 illustrates two ways to produce the starting material MTM SA and also shows various MTM SA derivatives.
Figure 3:
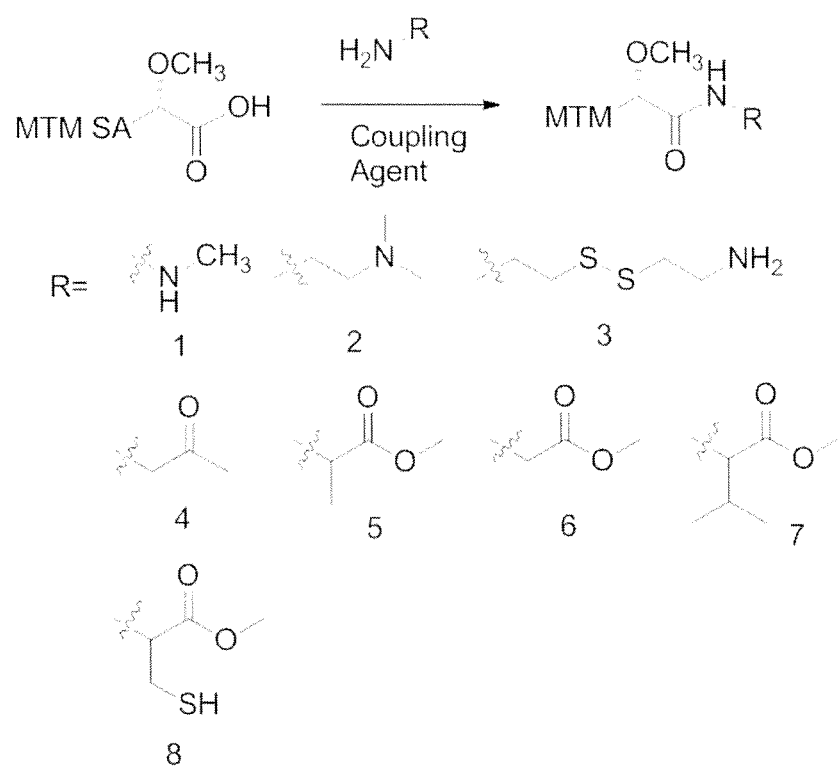
FIG. 3 illustrated functionalization of MTM SA through a reaction with a primary amine containing compound. Representative compounds are shown.

FIG. 2 illustrates two different ways to produce the starting material MTM SA and also shows various MTM SA derivatives. In the figure, the $MTM_1$ group can include different sugars or sugar chains, R represents a lower straight chain or branched alkyl unsubstituted or substituted with one or more amino, alkyl amino, alkylcarboxyl, alkoxyl, alkylcarbonyl, hydroxyl, thio, alkyldisulfide, halo other residues. In addition, the $NR_1R_2$ can form an amino acid conjugate or ester derivative thereof as shown in FIG. 2. In one aspect of the present disclosure, MTM SA amide derivatives can be prepared by coupling the terminal carboxylic acid group of MTM SA with an amine, e.g., a primary amine, to form the MTM SA derivative.

Examples of particular MTM SA derivatives together with their activity are provided in Table 2 in the Examples section below. Additionally, other amino acid derivatives of MTM SA can be prepared. For example, tryptophan can be substituted on the MTM SA derivative. The MTM SA-tryptophan derivative can be prepared the same way as the other amino acid derivatives, only using Tryptophan-O-methyl ester. OMe-Phe, OMe-Tyr and OMe-His derivatives can be prepared in the same manner.

The MTM SA derivatives of the present disclosure can be used for the treatment of cancer, such as brain, colon, prostate, lung, breast, esophageal, pancreatic, skin, Ewing sarcoma, any type of blood cancer etc. MTM derivatives are An aspect of the present disclosure involves targeting the 3-side chain of MTM SA to form useful MTM SA derivatives. It is known that the 3-side chain of the MTM structure is responsible for an interaction with the DNA-phosphate backbone. Thus by altering the functionality of the 3-side chain the specificity for the DNA of diseased cells can be improved. The 3-side chain of MTM SA is terminated by a carboxyl acid functional group which is likely ionized at a physiological pH, repulsing from the negative charge of the DNA phosphate backbone thereby weakening MTM SA's ability to bind to the DNA.

In one aspect of the present disclosure, side chain functionalizations were rationally selected to contain cationic amine residues in order to enhance the interaction with the DNA phosphate backbone.

Screening Methods

Figure 4:
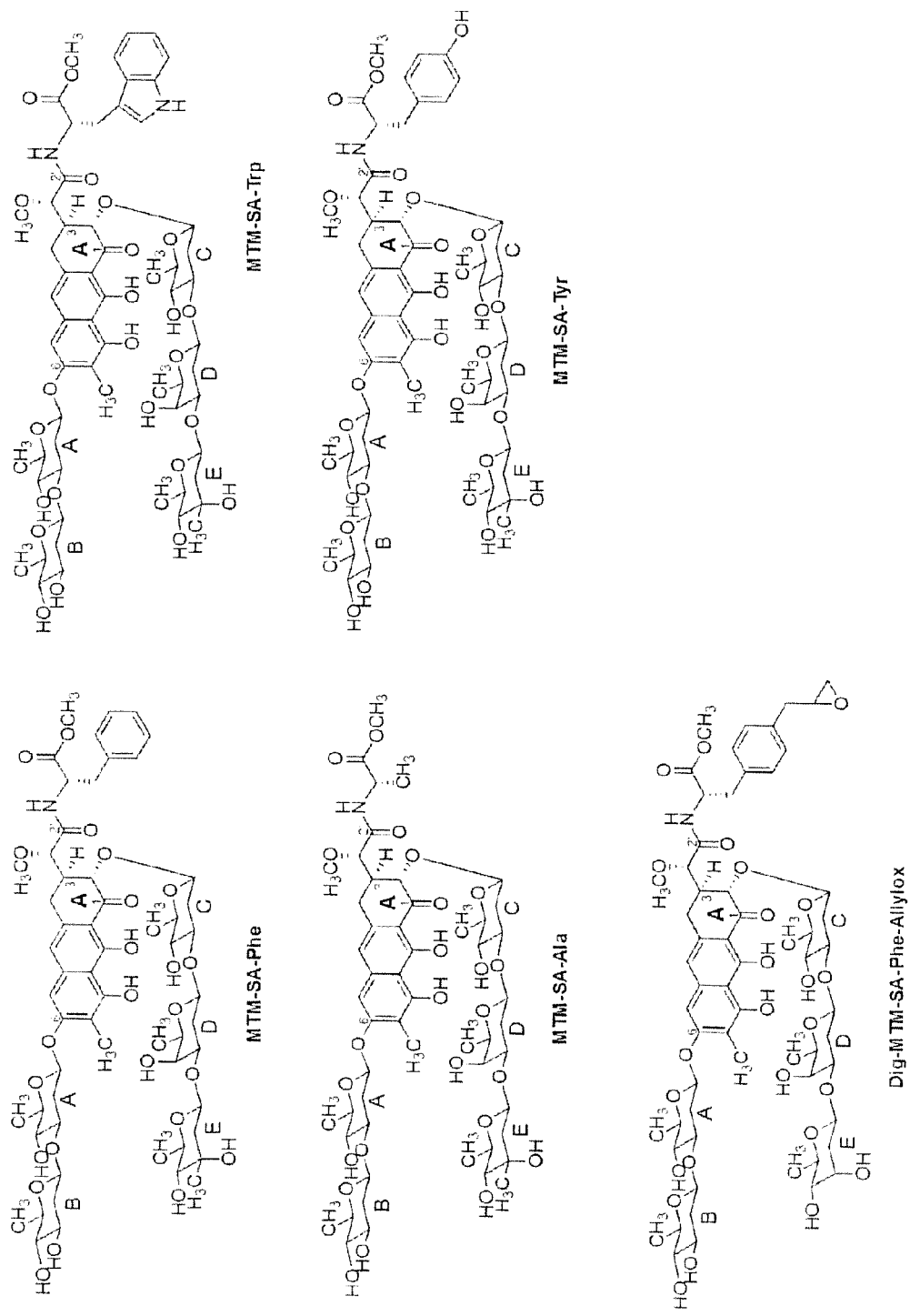
FIG. 4 illustrates five exemplary MTM SA derivatives that exhibit high specificity for EWS-FLI1 transcription factor in Ewing sarcoma.
Figure 5:
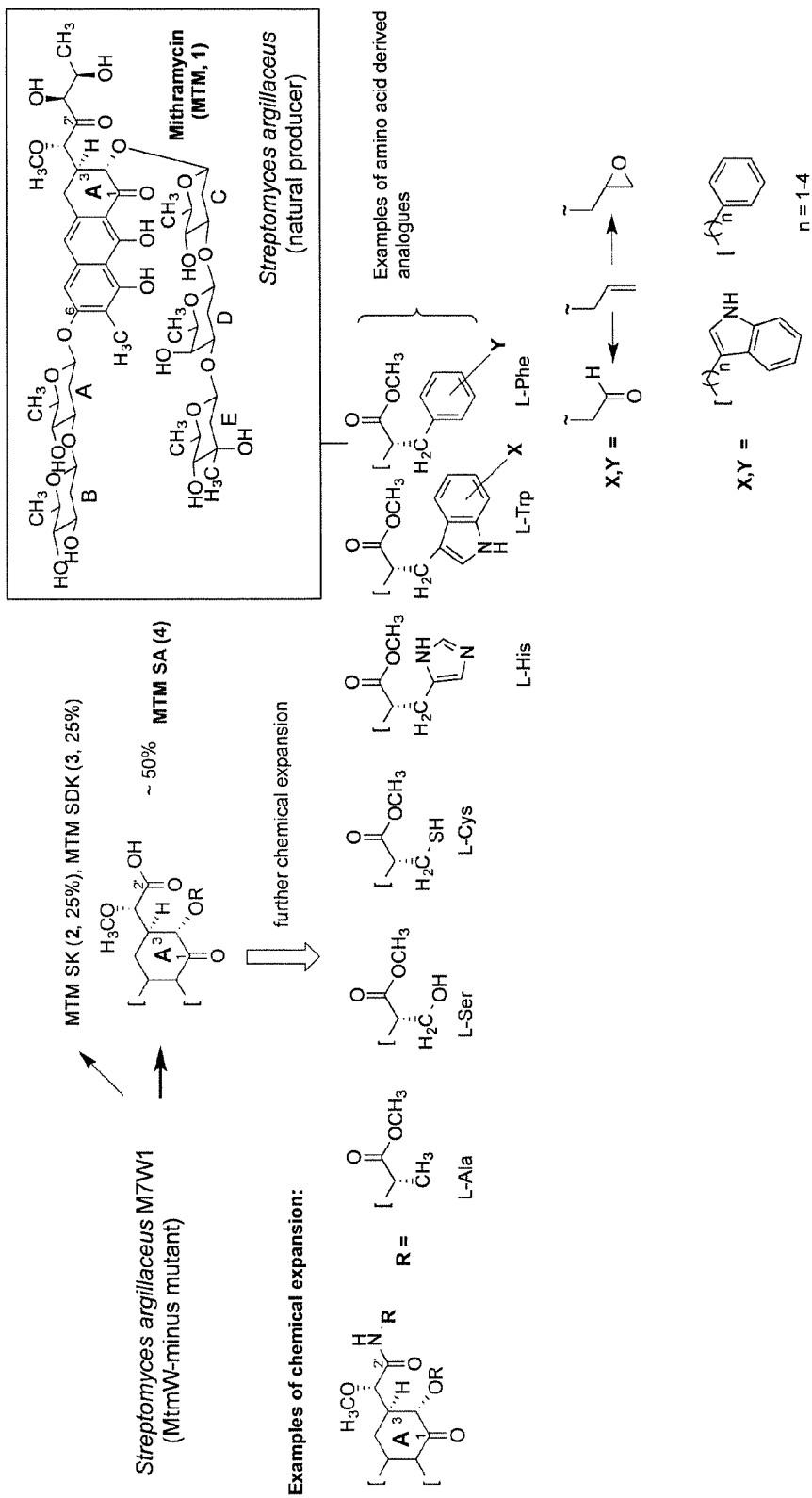
FIG. 5 illustrates certain MTM SA derivatives including substituted MTM SA-Trp and MTM SA-Phe.

The assay described herein provides a rational development and identification scheme for novel and potent MTM analogues and derivatives with improved selectivity against EWS-FLI1. Without wishing to be bound by a theory, the inventors have discovered inter alia that rather than displacing EWS-FLI1 from DNA, MTM binds DNA cooperatively with EWS-FLI1 and hyperstabilizes it on the DNA (FIG. 4), to disruption of its transcriptional functions residues in order to enhance the interaction with DNA phosphate backbone.

Accordingly, in one aspect the subject technology provides a screening assay for identifying MTM SA derivatives as test compounds that selectively and specifically bind to and modulate the activity of a target ETS transcription factor such as EWS-FLI1 transcription factor. The assay includes such steps as detecting the formation and/or stability of a complex that includes (1) a target ETS transcription factor that has a DNA binding domain with an amino acid sequence that is at least 85% identical to SEQ ID NO:01 or SEQ ID NO:02 over the entire length of either of these sequences, (2) an oligonucleotide substrate and (3) the test compound.

In some embodiments, the subject technology provides a method for screening mithramycin (MTM) derivatives including MTM SA or a pharmaceutically acceptable salt thereof for an ability to selectively complex with or modulate the activity of a target ETS transcription factor, said method including the steps of (a) contacting the MTM SA derivative with the target ETS transcription factor in the presence of an oligonucleotide substrate; (b) assessing the effect of the MTM SA derivative on the activity of the target ETS transcription factor; and (c) selecting the MTM SA derivative that has specificity for and/or modulates the activity of the target ETS transcription factor relative to a reference or control sample; wherein the target ETS transcription factor is Friend leukemia integration 1 transcription factor (FLI1) or v-ets avian erythroblastosis virus E26 oncogene-like transcription factor (ERG). In some related embodiments, the step (b) further includes assessing the formation of a complex comprising the MTM SA derivative, the target ETS transcription factor and the oligonucleotide substrate. In some related embodiments, the step of assessing the formation of the complex is performed by crystallography. In some related embodiments, the specificity of the test agent for the target ETS transcription is assessed by detecting the formation and/or stability of a complex formed between the target ETS transcription factor and its oligonucleotide substrate in the presence of the MTM SA derivative relative to a reference or control sample. In some related embodiments, the specificity of the test agent for the target ETS transcription is assessed by detecting the formation and/or stability of a complex including the target ETS transcription factor, the oligonucleotide substrate and the MTM SA derivative. In some related embodiments, the oligonucleotide substrate includes SEQ ID NOs:03-07. In some related embodiments, the oligonucleotide substrate is labeled with a detectable label. In some related embodiments, the MTM SA derivative or a pharmaceutically acceptable salt thereof is a compound described herein.

MTM SA-Phe is an exemplary MTM SA derivative that selectively and specifically binds to a target ETS transcription factor such as EWS-FLI1 is MTM SA-Phe which forms a ternary MTM SA-Phe:EWS-FLI1:DNA substrate complex that hyperstabilizes the transcription factor to its binding site, thus, perturbing the normal function of the transcription factor. Another such example is MTM SA-Trp.

According to some embodiments of the subject technology, the amount or stability of the complex in the presence of a test compound such as an MTM SA derivative is determined relative to a control or reference sample. A statistically significant increase in stability is indicative of an increase in the formation of the complex or an increase in the specificity of the test compound for the transcription factor. A control or reference sample can be one or more of a sample not exposed to the test compound; a sample exposed to known inhibitor of the target ETS transcription factor (e.g., FLI1 or ERG); a sample containing one or more other ETS transcription factors capable competing with the target ETS transcription factor for forming a complex with the test compound; a sample exposed to a known inhibitor of the complex; a sample containing a compound that may compete with the test compound to complex with the target ETS transcription factor; or a sample exposed to an excess amount of a labeled or an unlabeled binding member of the complex. Methods of determining formation and/or stability of the complex are described below.

According to some embodiments, the interactions between a target ETS transcription factor, its oligonucleotide substrate and an MTM SA derivative is fine-tuned by proper chemical modification of the MTM SA derivative to increase the specificity of the derivative for the target transcription factor. In some embodiments, the MTM SA derivative of the subject technology, while having high specificity for a target ETS transcription factor such as FLI1, will not displace the Sp transcription factors from the GC-rich promoter DNA. In the case of Ewing sarcoma, where the target ETS transcription factor is EWS-FLI1, the MTM SA derivative of the subject technology selectively complexes with and inhibits the activity of the EWS-FLI1 transcription factor and, thus, is a potent and selective anti-Ewing sarcoma therapy.

A variety of assay formats can be used and, in light of the present disclosure, those not expressly described herein will nevertheless be understood to be included by one of ordinary skill in the art. Screening methods or assay formats which approximate such conditions as formation of a ternary complex of a target ETS transcription factor (e.g., FLI1 or ERG):oligonucleotide substrate:MTM SA derivative can be generated in many different forms, and include assays based on cell-free systems, e.g., purified peptides and oligonucleotides or cell lysates, as well as cell based assays which utilize intact cells and in vivo assays.

The components of the complex can be added simultaneously to the assay sample, e.g., a reaction mixture or they can be added sequentially in any order, e.g., forming a mixture of the first component with a second component, adding the third component forming a mixture of the first, second, and third component, and adding the fourth component. In some embodiments, some components of the complex are added sequentially while others are added simultaneously, e.g., forming a reaction mixture with a first component with a second component and adding the third and fourth component simultaneously to the mixture, or adding a first component followed by simultaneous addition, e.g., a reaction mixture, of the rest of the components.

Assaying in the presence and absence of a test compound can be accomplished in any vessel suitable for containing the reactants. Examples include microtitre plates, test tubes, and micro centrifuge tubes. Alternatively, the sample can include cells in culture, e.g., purified cultured or recombinant cells, or in vivo in an animal subject.

In some embodiments, the screening assays can be performed in vitro using isolated/purified complex components. In such a system, each component of the screen can be added separately in wells of a multi-well plate. In some embodiments, the multimeric complex will be allowed to form prior to the addition of the test compound to be screened. In other embodiments, the members of the complex and the test agent will be added together, e.g., at the same time or simultaneously, with one or more of the members of the complex.

Complex components can be used at any concentration suitable for the assay conditions being used, e.g., size of the reaction vessel, time limitations, detection limits, amount of the limiting component, etc. Additionally, amount of the various components of the complex can be the same, all different, or combinations thereof. Generally, amount of each component is within 15% to 5% of the amount of each of the other components.

In some embodiments, the concentration of each of the complex components in the assay sample is independently from about 0.01 nM to about 1.0 mM. In some embodiments, the concentration of each of the complex components is independently from about 0.1 nM to about 100 µM, from about 0.5 nM to about 50 µM, or from about 1 nM to about 25 µM. In some embodiments, the concentration of each of the complex component is independently from about 10 nM to about 40 µM. In one embodiment, the concentration of each of the complex components is about 10 nM, or about 20 nM, or about 50 nM, or about 100 nM, or about 250 nM, or about 1 µM. In one embodiment, concentration of each of the complex component is greater than 20 nM.

The assay sample volume depends on the particular setup being used for the screening assay. Generally, the assay sample has a final volume of about 10 nl to about 1 ml. In some embodiments, the final volume of the sample assay is from about 1 ml to about 100 ml. In addition to the complex components, a variety of other reagents can be included in the screening assay samples. These include reagents like salts, neutral proteins, e.g., albumin, detergents, etc. that are used to facilitate optimal protein-protein binding and/or reduce nonspecific or background interactions. Reagents that improve the efficiency of the assay, such as protease inhibitors, single stranded nuclease inhibitors, anti-microbial compounds are also included. The mixture of components is added in any order that provides for the requisite assembly of the complex.

In some embodiments, the assay sample comprises a competitor of at least one component of the complex. The term "competitor of a component of the complex" refers to a compound or composition that competes with said component for binding with another component of the complex. For example, an unlabeled complex component can be considered a competitor of the labeled component. In another example, an oligonucleotide comprising either a target ETS transcription factor binding site or a transcription binding site is a competitor of the oligonucleotide substrate of the target ETS transcription factor. In some embodiments, the competitor is another ETS transcription factor other than, for example, a FLI1 or ERG. In another embodiment, the competitor is an MTM SA derivative other than the one being assayed.

The amount of a competitor of a component of the complex in the sample assay can be adjusted to optimize the detection of the assay. Accordingly, in some embodiments, concentration of the competitor in the assay sample is from about 0.01 nM to about 1000 nM. In some embodiments, amount of the competitor in the assay sample is from about 0.1 nM to about 100 µM, from about 0.5 nM to about 50 µM, or from about 1 nM to about 25 µM. In some embodiments, amount of the competitor in the assay sample is from about 10 nM to about 20 µM. In some embodiments, amount of the competitor in the assay sample is from about 150 nM to about 250 nM. In one embodiment, concentration of the competitor in the assay sample is about 10 nM, about 20 nM, or about 200 nM.

The amount of a competitor of a component of the complex in the sample assay can be relative to any other component of the complex. For example, the competitor can be present in an amount which is at least 0.1×, at least 0.2×, at least 0.3×, at least 0.4×, at least 0.5×, at least 0.6×, at least 0.7×, at least 0.8×, at least 0.9×, at least 1×, at least 1.25×, at least 1.5×, at least 1.75×, at least 2×, at least 2.5×, at least 3×, at least 4×, at least 5× or more relative to the amount of another complex component. In some embodiments, the competitor is present in an amount which is at least 0.1×, at least 0.2×, at least 0.3×, at least 0.4×, at least 0.5×, at least 0.6×, at least 0.7×, at least 0.8×, at least 0.9×, at least 1×, at least 1.25×, at least 1.5×, at least 1.75×, at least 2×, at least 2.5×, at least 3×, at least 4×, at least 5× or more relative to the amount of the complex component being competed against.

Any suitable buffer/media/solvent can be used in the screening assay. Exemplary buffers include, but are not limited to, phosphate buffered saline (PBS), sodium phosphate, sodium sulphate, Tris buffers, Tris-HCl buffers, glycine buffer, and sterile water. The buffer can be present in the assay sample at any suitable concentration. Typically, the assay sample comprises a buffer in a concentration of about 5-100 mM. In some embodiments, the assay sample comprises a buffer in a concentration of about 5-75 mM (e.g., 10 mM, 20 mM, 25 mM, 30 mM, 35 mM, 40 mM, 45 mM, or 50 mM). Generally, the buffer has a pH of from about 5 to about 10. In some embodiments, the buffer has a pH of from about 6 to about, from about 6.5 to about 8, or from 6.5 to about 7.5. The pH of the buffer can be adjusted by addition of any suitable acid or base (e.g., HCl). In some embodiments, the sample buffer is 20 mM Tris pH 7.5, 50 mM NaCl, 5% glycerol, 0.5 mg/ml BSA.

Formation and/or stability of the complex can be assayed at any suitable temperature. Accordingly, in some embodiments, the formation and/or stability of the complex is assayed at a temperature in the range of about 15° C. to about 65° C. In some embodiments, the formation and/or stability of the complex is assayed at a temperature in the range of about 15° C. to about 45° C. In some embodiments, the formation and/or stability of the complex is assayed at a temperature in the range of about 15° C. to about 25° C.

After all of the reagents have been added, evaluation of the complex formation or stability can be done right away, e.g., within 5 minutes of addition of last reagent, or after a period of time has elapsed after addition of the last reagent. In some embodiments, the sample assay is allowed to incubate for at least 5 minutes, at least 10 minutes, at least 15 minutes, at least 20 minutes, at least 25 minutes, at least 30 minutes, at least 35 minutes, at least 40 minutes, at least 45 minutes, at least 1 hour, at least 2 hours, at least 5 hours or more before evaluating the complex formation or stability. In one embodiment, the assay sample is allowed to incubate for 30 minutes after addition of the last reagent before evaluating the complex formation or stability.

The assays of the subject technology can be used to evaluate and/or detect a change in complex formation and/or complex stability by detecting one or more of (1) a change in the binding or physical formation of the complex itself, e.g., by biochemical detection, affinity based detection (e.g., Western blot, affinity columns), immunoprecipitation, fluorescence resonance energy transfer (FRET)-based assays (e.g., FRET or Time Resolved FRET (TR-FRET) assays), surface plasmon resonance (SPR), spectrophotometric means (e.g., circular dichroism, absorbance, and other measurements of solution properties); (2) an increase or a decrease, in signal transduction, e.g., phosphorylation and/or transcriptional activity; (3) an increase or decrease in cell function. All of these methods are known in the art.

In some embodiments, the screening assay is a high-throughput screening assay. HTS is a relative term, but is generally defined as the testing of 10,000 to 100,000 compounds per day, accomplished with mechanization that ranges from manually operated workstations to fully automated robotic systems using robotics, data processing and control software, liquid handling devices, and sensitive detectors.

Methods of Treatment

In one aspect, the subject technology provides a method for selectively modulating the activity of a target ETS transcription factor in a patient in need thereof, including administering to the patient a therapeutically effective amount of an MTM SA derivative or a pharmaceutically acceptable salt thereof having the following formula:

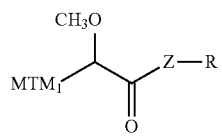

wherein Z represents O, S, N—R'; R and R' represent, for each occurrence, H, alkyl, heterocyclic, aryl, heteroaryl, provided that R is not H when Z is O; ZR taken together represents an organic residue; and wherein MTM$_1$ represents the fused ring portion of the mithramycin structure and can include different sugars or sugar chains. In addition, Z and R can represent all of the various embodiments described herein including when ZR together form an amide, amino acid conjugate or ester derivative thereof, etc.

In an embodiment relating to this aspect, the subject technology provides a method for selectively modulating the activity of a target ETS transcription factor in a patient with Ewing sarcoma or prostate cancer for example. The method includes administering to the patient a therapeutically effective amount of MTM SA-Phe or MTM SA-Trp, or a derivative thereof, for example. In some embodiments relating to this aspect, the ETS transcription factor includes a DNA binding domain with an amino acid sequence that is at least 85% identical to SEQ ID NO:01 or SEQ ID NO:02 over the entire length of either of these sequences. In other embodiments relating to this aspect, ZR together represents an NR$_1$R$_2$ group, e.g., an amino acid conjugate or an ester derivative thereof. In certain embodiments, NR$_1$R$_2$ is the amino acid conjugate is an aromatic amino acid conjugate, e.g., phenylalanine, tryptophan or an ester derivative thereof. The amino acid conjugate or ester derivative thereof can further be substituted. Substituents include, for example, —R$_3$Y where R$_3$ is alkyl, e.g., C$_{1-16}$ or C$_{1-8}$ alkyl, and Y is a formyl ene, expoxy, aryl, e.g., phenyl, heteroaryl, e.g., indolyl. In some embodiments —R$_3$Y together form an allylox group. In other embodiments relating to this aspect, the MTM SA derivative includes one or more sugar groups such as D-digitoxose. In other embodiments relating to this aspect, the MTM SA derivative is MTM SA-Phe or MTM SA-Trp and the target ETS transcription factor being selectively modulated is FLI1 and/or ERG. In other embodiments relating to this aspect, the MTM SA derivative is MTM SA-Phe which further includes one or more different sugar groups such as D-digitoxose and/or an indole ring on the phenylalanine and the target ETS transcription factor being modulated is FLI1 and/or ERG. In other embodiments, the MTM SA derivative is MTM SA-Phe-Allylox and the target ETS transcription factor being selectively modulated is FLI1 and/or ERG. In other embodiments relating to this aspect, the MTM SA derivative is MTM SA-Phe-Allylox which further includes one or more different sugar groups such as D-digitoxose and the target ETS transcription factor being modulated is FLI1 and/or ERG.

In other embodiments relating to this aspect, the MTM SA derivative is MTM SA-Phe or MTM SA-Trp and the target ETS transcription factor being selectively modulated is FLI1 and/or ERG. In other embodiments relating to this aspect, the MTM SA derivative is MTM SA-Phe or MTM SA-Trp which further include one or more different sugar groups such as D-digitoxose and the target ETS transcription factor being modulated is FLI1 and/or ERG. In other embodiments, administration results in modulation of the activity of the ETS transcription factor in the patient. In other embodiments, the target ETS transcription factor is Friend leukemia integration 1 transcription factor (FLI1) or v-ets avian erythroblastosis virus E26 oncogene like transcription factor (ERG).

In another aspect, the subject technology provides a method of treating a target ETS transcription factor-mediated disease in a patient by administering to the patient a therapeutically effective amount of an MTM SA-Phe, MTM SA-Trp or any other MTM SA derivative described herein, wherein the MTM SA derivative specifically modulates the activity of the ETS transcription factor mediating the disease and wherein the target ETS-mediated disease is Ewing sarcoma, clear-cell sarcoma, myxoid liposarcoma, desmoplastic small round cell tumor, myxoid chondrosarcoma, acute myeloid leukemia, congenital fibrosarcoma, prostate cancer or pancreatic cancer, for example. Table 1 below lists several ETS transcription factors that may be modulated and associated diseases that may be treated with the subject technology.

TABLE 1

ETS Transcription factors and associated diseases.

| Transcription factor | Disease |
| --- | --- |
| ETS-1 | Meningioma, invasive carcinoma of the breast, colorectal carcinoma, pancreatic carcinoma, adenocarcinoma, thyroid carcinoma, thymoma, angioma |
| ETS-2 | Breast cancer |
| ERG | TMPRSS2:ERG fusion in prostate cancer EWS-ERG fusion in Ewing Sarcoma ERG overexpression in AML |
| FLI1 | EWS-FLI1 fusion in Ewing Sarcoma |
| PEA3 | Invasive breast carcinoma |
| ER81 | EWS-ER81 fusion in Ewing sarcoma, prostate carcinoma, breast carcinoma |
| ELF-1 | Prostate, ovarian and breast cancers, leukemia and lymphoma. |
| TEL/ETV6 | TEL fusion protein partners (PDGFbetaR, TRKc, ABL, and JAK2) in leukemia and fibrosarcoma |
| PU.1/SPI1 | Promyelocytic leukemia, acute myelocytic leukemia |
| Myc | Burkitt lymphoma, B-cell lymphoma, multiple myeloma, medulloblastoma, neuroblastoma, colorectal, ovarian and intestinal cancer |

The target ETS transcription factor specifically modulated may be FLI1 transcription factor or ERG transcription factor. In an embodiment of this aspect, a therapeutically effective amount of MTM SA-Trp or MTM SA-Phe or a derivative or salt thereof is administered to a Ewing sarcoma patient. In other embodiments, a therapeutically effective amount of MTM SA-Trp or MTM SA-Phe or a derivative or salt thereof is administered to a patient with any of the diseases listed in Table 1.

In general, the MTM SA derivatives of the present disclosure can be used for the treatment of a target ETS transcription factor-mediated disease including Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblatic leukemia (ALL), Alzheimer's disease (AD), or Down syndrome (DS) or other hyperproliferative disease in which an aberrant activity of a target ETS transcription factor is implicated. A "hyperproliferative disease" includes diseases and conditions that are associated with any sort of abnormal cell growth or abnormal growth regulation, specifically a cancer.

In certain embodiments, the present disclosure provides a method of treating a hyperproliferative disease mediated by an aberrant activity of a target ETS transcription factor comprising administering to a subject in need thereof a therapeutically effective amount of a composition comprising an MTM SA derivative such that the activity of the target transcription factor is reduced or inhibited; wherein the MTM SA derivative is MTM SA-Phe, MTM SA-Trp, MTM SA-Ala, MTM SA-Tyr or MTM SA-Phe-Allylox and wherein the target ETS-mediated disease is Ewing sarcoma, clear-cell sarcoma, myxoid liposarcoma, desmoplastic small round cell tumor, myxoid chondrosarcoma, acute myeloid leukemia, congenital fibrosarcoma, prostate cancer or pancreatic cancer. In certain other embodiments, the present disclosure provides a method of treating Ewing sarcoma comprising administering to a subject in need thereof a therapeutically effective amount of a composition comprising an MTM SA derivative selected from the group consisting of MTM SA-Phe, MTM SA-Trp, MTM SA-Ala, MTM SA-Tyr, MTM SA-Phe-Allylox or a derivative thereof, wherein the derivative comprises one or more sugar groups comprising digitoxos or other derivative described herein. In an embodiment of this aspect, the target ETS transcription factor specifically modulated is Friend leukemia integration 1 transcription factor (FLI1) or v-ets avian erythroblastosis virus E26 oncogene-like transcription factor (ERG). In an embodiment, the present disclosure provides a method of treating a hyperproliferative disease mediated by an aberrant activity of a target ETS transcription factor comprising administering to a subject in need thereof a therapeutically effective amount of a composition comprising MTM SA-Phe and/or MTM SA-Phe allylox or comprising MTM SA-Trp such that the activity of the target transcription factor is reduced or inhibited; wherein the ETS target transcription factor is FLI1 or ERG.

As described above, the screening method of the subject technology identifies MTM SA derivatives that are more specific than MTM for complexing with a target EST transcription factor and, therefore, inhibiting its activity. The specific or selective MTM SA derivatives of the subject technology are useful for treating diseases that are mediated by, for example, FLI1 or ERG, such as Ewing sarcoma, clear-cell sarcoma, myxoid liposarcoma, desmoplastic small round cell tumor, myxoid chondrosarcoma, acute myeloid leukemia, congenital fibrosarcoma, prostate cancer, pancreatic cancer, acute myeloid leukemia (AML), acute lymphoblatic leukemia (ALL), Alzheimer's disease (AD), or Down syndrome (DS) or other hyperproliferative disease in which an aberrant activity of a target ETS transcription factor is implicated.

Other hyperproliferative diseases which may be benefited by the methods and compounds of the subject technology include, though it is not limited to, neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In another aspect of the present disclosure, an effective amount of the MTM SA derivative or a pharmaceutically acceptable salt thereof is administered to a patient in need of cancer treatment or a neuro-disease, such as Huntington'd disease. The MTM SA derivatives or pharmaceutically acceptable salts thereof of the present disclosure can be administered to a patient, e.g., a human patient, in need of such treatment by any route. The MTM SA derivatives or pharmaceutically acceptable salts thereof of the present disclosure can be administered alone or with a pharmaceutically acceptable carrier or excipient.

Dosage Form and Formulation of MTM SA

An MTM SA derivative of the subject technology such as MTM SA-Phe, MTM SA-Trp or a derivative thereof can be administered to a patient in need thereof in any possible dosage form including, but not limited to ingestible tablets, buccal tablets, troches, capsules, elixirs, suspensions, syrups, wafers, infusion, aqueous liquid and the like. Solutions of an MTM SA such as MTM SA-Phe or MTM SA-Trp can be prepared in water and mixed with suitable excipients. Under ordinary conditions of storage and use, these preparations can contain a preservative to prevent the growth of microorganisms or retain stabilization of the MTM SA derivative. The pharmaceutical forms suitable for injection include sterile aqueous solutions or dispersions and sterile powders for the extemporaneous preparation of sterile injectable solutions or dispersions. The form should be sterile and should be fluid to the extent it makes injection possible.

A composition containing an MTM SA derivative of the disclosure such as MTM SA-Phe, MTM SA-Trp or a pharmaceutically acceptable salt thereof can be prepared by known methods, such that an effective quantity of the therapeutic agent is delivered to a subject. Suitable vehicles for such a composition are described, for example, in Remington's Pharmaceutical Sciences (2003) and in the Handbook of Pharmaceutical Additives (compiled by Michael and Irene Ash, Gower Publishing Limited, Aldershot, England (1995)).

In some embodiments, the composition of this disclosure enables sustained, continuous delivery of an MTM SA derivative such as MTM SA-Phe, MTM SA-Trp or a pharmaceutically acceptable salt thereof to tissues adjacent to or distant from an administration site. The biologically-active agent is capable of providing a local or systemic biological, physiological or therapeutic effect. For example, MTM SA-Phe or MTM SA-Trp may act to kill cancer cells or cancer stem cells or to control or suppress tumor growth or metastasis, among other functions.

In some embodiments, the formulations of the present disclosure are administered in an amount effective to provide the desired level of biological, physiological, pharmacological and/or therapeutic effect such as inhibition of a target ETS transcription factor.

The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical formulations include, for example, at least about 0.1% of an active compound, such as MTM SA or derivatives thereof or pharmaceutically acceptable salt thereof. In other embodiments, the active compound may comprise between about 1% to about 75% of the weight of the unit dosage, or between about 5% to about 50% by weight of the unit dosage, for example, and any specific percentage in between these ranges. In other non-limiting examples, a dose may also comprise from about 0.01 microgram/kg/body weight, about 50 microgram/kg/body weight, about 100 microgram/kg/body weight, about 500 microgram/kg/body weight, about 1 milligram/kg/body weight, about 5 milligram/kg/body weight, about 10 milligram/kg/body weight, about 30 milligram/kg/body weight, about 40 milligram/kg/body weight, about 50 milligram/kg/body weight, about 100 milligram/kg/body weight, or more per administration, and any range or specific amount derivable therein. In non-limiting examples of a derivable range from the numbers listed herein, a range of about 5 microgram/kg/body weight to about 5 milligram/kg/body weight, about 50 microgram/kg/body weight to about 50 milligram/kg/body weight, etc., can be administered.

For a safe and effective dosage, the formulations can be administered at an MTM SA derivative dose of about 0.01 to about 500 mg/m$^2$ (body surface)/day, about 0.01 to about 300 mg/m$^2$/day, 0.01 to about 200 mg/m$^2$/day, about 1 to about 200 mg/m$^2$/day about 10 to about 100 mg/m$^2$/day, about 25 to about 100 mg/m$^2$/day or any range derivable therein to a subject such as a human. In certain aspects, the composition may be administered at a dose of about 0.01 to about 200 mg/kg body weight, about 0.01 to about 100 mg/kg body weight, 1 to about 50 mg/kg body weight, about 1 to about 20 mg/kg body weight, about 3 to about 10 mg/kg body weight, about 3 to about 6 mg/kg body weight or any range derivable therein to a subject such as a human. In some embodiments, a formulation of the subject technology may be administered in a dose of 1, 2, 3, 4, 5, 6, 7, 8, 9, 10, 15, 20, 25, 30, 40, 50, 60, 70, 80, 90, 100 mg or more per day. Each liquid dose may be in a volume of 1, 10, 50, 100, 200, 500, 1000 or more μl or ml.

In some embodiments, the pharmaceutical formulation of the subject technology includes an MTM SA derivative such as MTM SA-Phe or MTM SA-Trp in an amount effective to result in a serum concentration of the MTM SA in the mammal in a range of from 1 nM to 1 mM, particularly 1 nM to 2 μM.

Serum and systemic circulation concentrations of MTM SA derivatives effective to result in the treatment of a target ETS transcription factor-mediated disease may vary depending on a number of factors. Influential variables can include, for example, pKa, solubility or molecular weight of the MTM SA derivative. These properties of a particular MTM SA derivative such as MTM SA-Phe or MTM SA-Trp may affect how a patient metabolizes the compound, how much of the compound enters and remains in the systemic circulation of the patient, and how effectively the compound treats, prevents or causes regression of the disease, e.g., Ewing sarcoma, tumor or cancer.

Precise amounts of the therapeutic composition also depend on the judgment of the practitioner and are peculiar to each individual. Factors affecting the dose include the physical and clinical state of the patient, the route of administration, the intended goal of treatment (e.g. alleviation of symptoms versus cure) and the potency, stability and toxicity of the particular therapeutic substance.

Route of Administration

In accordance with the methods of the disclosure, the described composition or formulation of the subject technology may be administered to a subject in a variety of forms depending on the selected route of administration, as will be understood by those skilled in the art. It may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, intratumoral, transepithelial, nasal, intrapulmonary, intrathecal, rectal and topical modes of administration. Parenteral administration may be by continuous infusion over a selected period of time.

Combination Therapies

In certain embodiments, the compounds, compositions or formulations of the subject technology are administered with a second or additional active agent(s) such as with one or more different MTM SA derivatives or another anticancer agent. Such therapy can be applied in the treatment of any disease for which treatment with an MTM SA derivative such as MTM SA-Phe or MTM SA-Trp is contemplated. For example, the disease may be a hyperproliferative disease, such as Ewing sarcoma or prostate cancer.

In certain embodiments, the additional active agent may be a chemotherapeutic agent or a radiation therapy. Examples of chemotherapeutic agents include, but are not limited to, cetuximab (erbitux), herceptin (trastuzumab), fludarabine, cyclophosphamide, rituximab, imatinib, Dasatinib (BMS0354825), cisplatin (CDDP), carboplatin, procarbazine, mechlorethamine, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol, gemcitabien, navelbine, farnesyl-protein tansferase inhibitors, transplatinum, 5-fluorouracil, vincristin, vinblastin, methotrexate, an analogue or derivative thereof. In certain embodiments, the active or anticancer agent(s) that may be used in combination with an MTM SA derivative may be fludarabine, cyclophosphamide, rituximab, imatinib or Dasatinib. In a certain aspect, the cancer may be resistant to a particular chemotherapeutic agent, such as fludarabine, cyclophosphamide, rituximab, imatinib or Dasatinib.

Polypeptides

In some embodiments, the subject technology provides an engineered ETS transcription factor comprising a DNA binding domain of SEQ ID NO:01 or SEQ ID NO:02, wherein the ETS transcription factor includes at least one amino acid substitution at any of amino acid residues corresponding to residues Tyr68, Lys75, His77, Gly78, Lys79, Arg80, Tyr81, Ala82 of its DNA binding domain. In some other embodiments, the subject technology provides an engineered ETS transcription factor comprising a DNA binding domain with an amino acid sequence that is at least 85% identical to SEQ ID NO:01 or SEQ ID NO:02 over the entire length of either of these sequences, and has at least one amino acid substitution at any of the amino acid residues of its DNA binding domain that correspond to residues Tyr68, Lys75, His77, Gly78, Lys79, Arg80, Tyr81, Ala82 of SEQ ID NO:01 or SEQ ID NO:02.

The engineered ETS transcription factors of the subject technology may be prepared in a number of ways that are known by a person skilled in the art. For example, mutations may be introduced by means of oligonucleotide-directed mutagenesis or other conventional methods. Alternatively, engineered ETS transcription factors may be generated by site specific replacement of a particular amino acid with an unnaturally occurring amino acid. This may be achieved by growing a host organism capable of expressing either the wild-type or mutant polypeptide on a growth medium depleted of one or more natural amino acids but enriched in one or more corresponding unnaturally occurring amino acids. The expression or the activity (e.g., DNA binding) of the engineered polypeptide may be determined using the methods described in the Examples.

For increased stability and half-life, the engineered polypeptides of the subject technology may be modified by chemical moieties and/or functional groups such as an amine, carboxyl, thiol or hydroxyl group. See, e.g., Kochendoerfer et al., Science, 299: 884-887 (2003) which is incorporated herein by reference in its entirety. Chemicals useful in making such modifications include, but are not limited to, polymers like polyethylene glycol (PEG), polypeptides such as the Fc portion of an antibody or chemical groups. These modifications will increase the stability and half-life of the polypeptides of the subject technology.

Polynucleotides

Another aspect of the subject technology provides polynucleotide sequences encoding the engineered ETS transcription factors of the subject technology. Further included in the subject technology are polynucleotides encoding the engineered ETS transcription factors of the present disclosure that are fused in frame to the coding sequences for additional heterologous amino acid sequences. Also included are nucleic acids encoding the engineered ETS transcription factors of the present disclosure together with additional, non-coding sequences, including, but not limited to, non-coding 5' and 3' sequences, vector sequence, sequences used for purification, probing, or priming. For example, heterologous sequences include transcribed, untranslated sequences that may play a role in transcription and mRNA processing, such as ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification or detection of the fused polypeptide. In certain embodiments of this aspect of the subject technology, the tag amino acid sequence is a hexa-histidine peptide (SEQ ID NO: 10), such as the tag provided in a pQE vector (QIAGEN), or in any of a number of additional, commercially available vectors.

Polynucleotides of the subject technology will be generally at least 60% or 70%, preferably at least 80 or 90% and more preferably at least 95% or 98% homologous to the nucleotide sequences encoding an engineered ETS transcription factor described above, over a region of at least 20, preferably at least 25 or 30, for instance at least 40, 60 or 100 or more contiguous nucleotides. Polynucleotides of the subject technology will be capable of encoding an engineered ETS transcription factor with a DNA binding domain comprising a DNA binding domain with an amino acid sequence that is at least 85% identical to SEQ ID NO:01 or SEQ ID NO:02 over the entire length of either of these sequences and has at least one amino acid substitution at any of amino acid residues corresponding to residues Tyr68, Lys75, His77, Gly78, Lys79, Arg80, Tyr81, Ala82 of SEQ ID NO:01 or SEQ ID NO:02.

Constructs

In another aspect of the subject technology, the coding polynucleotide sequences encoding the engineered ETS transcription factors of the subject technology may be operably linked to a promoter in a DNA construct using conventional cloning technology. The promoter may be a homologous or a heterologous promoter, i.e., a promoter not natively associated with the coding sequence. The promoter may be constitutive or inducible. Suitably, the promoter includes an expression control sequence near the start site of transcription. A promoter may include enhancer or repressor elements that may be non-contiguous with the start site of transcription. The polynucleotide may be provided within a vector, for example, a plasmid, cosmid, or virus.

Kits

The subject technology also encompasses kits for assessing the effect of a test agent, i.e., an MTM SA derivative or a pharmaceutically accepted salt thereof, on the activity of target ETS transcription factor or its complex formation with a DNA substrate and the test agent. In some embodiments, the kit comprises a detectably labeled or unlabeled test agent and/or a detectably labeled or unlabeled DNA substrate and/or a detectably labeled target ETS transcription factor such as FLI1 or ERG. The kit can further comprise instructions for using the kit to detect target protein or nucleic acid. In particular, the kit comprises an engineered ETS transcription factor comprising a DNA binding domain of SEQ ID NO:01 or SEQ ID NO:02, wherein the transcription factor includes at least one amino acid substitution at any of amino acid residues corresponding to residues Tyr68, Lys75, His77, Gly78, Lys79, Arg80, Tyr81, Ala82 of SEQ ID NO:01 or SEQ ID NO:02.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Example 1

Biosynthesis of MTM SA Derivatives

Materials and Methods

N,N'-diisopropylcarbodiimide (DIC), N-hydroxysuccinimide (NHS), dimethylformamide (DMF), dichloromethane (DCM), O-(Benzotriazol-1-yl)-N,N,N',N''-tetramethyluronium tetrafluoroborate (TBTU), COMU, diphenyl phosphoryl azide (DPPA), N,N-diisopropylethylamine (DIPEA), methyl hydrazine, benzotriazol-1-yl-oxytripyrrolidinophosphonium hexafluorophosphate (PyBOP), L-cysteine methyl ester hydrochloride, L-glycine methyl ester hydrochloride, L-alanine methyl ester hydrochloride, L-valine methyl ester hydrochloride, cystamine, DMSO (molecular biology grade, 99.9%), dimethylsulfoxide-$d_6$ (DMSO-$d_6$), resazurin sodium salt, were purchased from Sigma-Aldrich (USA). N,N-dimethylethylenediamine was purchased from TCI America (USA). 1-amino-2-propanone was purchased from Waterstone Tech (USA). Methanol (MeOH), acetonitrile (ACN), celite, C18 RP silica gel, tryptic soy broth (TSB), LB broth, Difco agar, sucrose, potassium sulfate, magnesium chloride, glucose, casamino acids, yeast extract, MOPS, and trace elements were purchased from Fisher Scientific (USA). *Streptomyces argillaceus* ATCC 12956, A549 tissue culture cells, F-12K media, fetal bovine serum (FBS) were purchased from ATCC (USA).

Biosynthesis of MTM SA

MTM SA was produced by an adapted procedure reported previously. *S. argillaceus* M7W1 was plated on R5A agar and allowed to grow for four days or until spores formed. The spores were then used to seed a culture in 100 mL of tryptic soy broth (TSB) and grown for 24 hr in an orbital shaker at 28° C., 250 rpm. After 24 hrs 4 mL of the TSB culture was used to start a culture in R5A media in 40, 100 mL flasks. The cultures in R5A media were grown for 3 days at 28° C., 250 rpm while the production of SA was monitored by HPLC. After 3 days the cells were collected with 50 g/L of celite and removed by filtration. The cell pellet was then re-dissolved in MeOH and sonicated for 1 hr to lyse the cells. Following the cell lysis the cellular debris was filtered off and the MeOH was evaporated from the filtrate. The dried cellular extract was then reconstituted in water and loaded onto a 5×12 cm C18 RP column equilibrated with 10 column volumes of water. The column was washed with 10% ACN in water, followed by a fractionation of ACN in water from 20-50%, followed by 100% ACN. The filtrate removed from the cells in step one was added to the C18 column and eluted by the same fractionation procedure. The samples were dried and re-constituted in 80% MeOH and water. SA was then completely isolated from the mixture of a few compounds by semi-preparative HPLC.

Synthetic Modification of MTM SA 3 Side Chain

MTM SA was modified by converting the terminal carboxylic acid group with a primary amine through a coupling reaction. Several different protocols were investigated to discover the optimal reaction conditions. For all of the exploratory reactions 2 mg of MTM SA was used. The initial reaction was completed by reacting MTM SA with the desired side chain modifying molecule in a 3× molar ratio, 3×DIPEA and 1×TBTU in 500 DCM starting at 4° C. The reaction was monitored at 2 h by HPLC-MS and allowed to proceed a total 24 h with the products analyzed by HPLC-MS. For HPLC-MS analysis a small aliquot was removed from the reaction mixture, the solvent dried off, and then reconstituted in methanol for analysis. For the initial reaction an extract on with ethyl acetate and the separation of the aqueous and organic phase was attempted, however this was not repeated with the subsequent reactions. The reaction was then repeated with 3×DIPEA, 10× of the side chain modification molecule, and 2× of the coupling agent DPPA in DMF, starting at 4° C. and monitored at 24 and 36 h. The protocol was modified and optimized by returning to 3× of the desired side chain modification molecule and while substituting the coupling agents COMU or PyBOP and the solvent DCM or DMF in different combinations. The reactions were checked at 24 and 48 h. After the reactions were completed the solvent was removed and the product mixture was reconstituted in methanol. The mixture was analyzed by HPLC-MS using a combination of the mass and UV absorbance to identify the elution peaks corresponding to the expected products. HPLC was then used to isolate the individual compounds. The organic solvents were removed from the samples followed by the freeze drying of the compounds. To scale up the production of the compounds 10 mg of SA was reacted with 3× of the side chain molecule, 3×DIPEA, 2× PyBOP in DCM, starting at 4° C., for 24 h. The solvent was removed and the products were reconstituted in methanol and isolated by HPLC. The side chain modification molecules included methyl hydrazine, L-cysteine methyl ester, L-glycine methyl ester, L-alanine methyl ester, L-valine methyl ester, cystamine, N,N-dimethylethylenediamine, and 1-amino-2-propanone (FIG. 2).

Structure Confirmation

The structures of the most active derivatives from the reactions with MTM SA and L-glycine methyl ester, L-alanine methyl ester, and L-valine methyl ester were confirmed through $H^1$ and $C^{13}$ NMR along with MALDI-TOF mass spectrometry performed by the University of Kentucky Mass Spectrometry Facility. The NMR measurements were taken on a 500 MHz NMR in methanol-d4

In Vitro Cytotoxicity Assays

The cytotoxic effects of the side chain modifications of SA were investigated in order to determine whether the modification were beneficial to the drug structure. All cytotoxicity assays were performed with A549, human non-small cell lung cancer cells. A549 cells were cultured as specified from ATCC at 37° C., 5% $CO_2$. The cells were added to a 96 well plate (5,000 cells/well) and permitted to attach for 24 h. After 24 h culture media were replaced with the side chain modified MTM SA derivative containing media at differing concentrations. The cells were incubated with the drug containing media for 72 hrs total (n=8). Cell viability was determined using a resazurin assay that signifies mitochondrial metabolic activity in living cells. 10 pL of a 1 mM resazurin solution in PBS was added to the control and analogue-treated cells at the end of the treatment period. Cell viability was determined three hours later by reading the fluorescence at 560 nm (Ex)/590 nm (Em). The fluorescence signals were quantified using a Spectramax M5 plate reader (Molecular Devices) equipped with a SoftMaxPro software. Cytotoxicity was determined by calculating the half maximal inhibitory concentration ($IC_{50}$) of each sample.

Biotechnological Production of MTM SA

MTM SA was successfully produced by the *S. argillaceus* M7W1 and isolated through an adapted procedure developed previously. Spores of *S. argillaceus* were formed by plating the cells of the M7W1 mutant strain on R5A agar and allowing them to grow until spores were formed. Colonies of the *S. argillaceus* cells began to appear after incubation for two days and after three days spores were observed. The cells were allowed to incubate for one more day to allow the majority of the cells to exist as spores and then added to TSB media. Once transferred to the TSB the cells grew quickly and after 24 h the TSB culture was used to inoculate multiple flasks of R5A media to produce SA. The pH of the R5A media was adjusted to pH 6.85. HPLC was used to monitor the culture for the production of SA. After 72 h the culture production was primarily composed of the end products including MTM SK and MTM SDK in addition to MTM SA, and the culture was terminated. A large portion of the MTM SA production is excreted into the culture media so once the culture process was stopped the media and the cells were separated. Celite cell binding resin was used to bind the cells and allow the culture to more easily be separated through filtration. C18 RP silica gel was able to successfully collect MTM SA from the complex culture mixture. Other compounds were also collected by the column so initial washes of 10% and 20% ACN were used to remove many of the byproducts from the sample. Further fractionation of the culture on the C18 RP column in addition to the loading and subsequent fractionation on a new, smaller C18 RP column did not aid in the isolation of MTM SA from the other MTM analogues so all compounds were eluted to together with 100% ACN to minimize dilution. There was also still some MTM SA contained inside the cells removed in the initial filtration step so the cells were lysed by sonication in methanol to release the intracellular content including all the MTM SA. Filtration removed the cellular debris, followed by the removal of the methanol. The same procedure as with the culture media then resulted in a relatively simple mixture of MTM SA along with the other MTM analogues and a few other impurities. Since the fractionation of the sample on the C18 RP silica gel did not completely isolate MTM SA from the other analogues the final purification steps were performed by using semi-preparative HPLC. The individual peak corresponding to MTM SA was collected and analyzed for purity using HPLC-MS. MTM SA was able to be collected at >95% purity and was stored at 20° C. until further use.

Synthetic Modification of MTM SA 3 Side Chain (1)

Once produced, MTM SA was modified chemically by taking advantage of the terminal carboxylic acid on the 3-side chain of the molecule. Several different protocols were attempted in order to discern the most favorable reaction conditions. The reactions were monitored by HPLC and the ratio of the signal corresponding to MTM SA was compared to the appearance of any new peaks following the reaction. MTM SA eluted with a retention time of 16.5 min, showing absorption of 410 nm and a mass to charge ratio of m/z 1026. The initial reaction with methyl hydrazine and TBTU as a coupling agent in DCM only displayed SA as the major component of the mixture after 2 h with only very minor other peaks appearing. After 24 h the MTM SA peak was gone with several broad peaks with shorter retention times appeared. The initial attempt to separate the products by ethyl acetate extraction did not result in favorable results and thus was not repeated. The reaction was then repeated with methyl hydrazide with the DPPA coupling agent in DMF. The reaction was also performed with 1-amino-2-propanone under the same conditions. After 24 h a new peak at 14.0 min appeared equal in intensity to that of the MTM SA peak. The expected product had a m/z of 1054.4, the same as the 14.0 min peak of 1054.4. The absorption of the peak was shifted however to 440 nm. The reaction with the 1-amino-2-propanone did not produce a new peak even after 36 hrs. The reaction was then repeated using the coupling agent COMU in DMF with the side chains L-glycine methyl ester hydrochloride and N,N-dimethylethylenediamine. For the reaction with N,N-dimethylethylenediamine a new product appeared with a retention time of 11.25 min, a UV-Vis absorption of 410 nm and a m/z matching that of the expected product of 1096.6 (1096.5 expected). For the reaction with L-glycine methyl ester hydrochloride three new products were formed with retention times of 14.4, 15.6, and 17.0 min. The UV-Vis absorption for the peaks were 455 nm, 455 nm, and 410 nm with 1097.3, 1168.4, and 1097.3 m/z, respectively. The calculated m/z for the correct product of the reaction with L-glycine methyl ester hydrochloride is 1097.4 m/z. There was still also a small peak corresponding to MTM SA. The reaction of MTM SA with cystamine was performed in DMF with COMU and resulted in the formation of a new peak at 9.0 min with absorption of 455 nm and m/z 1160.6. The theoretical m/z of the expected product was 1085.8 but if a disulfide bond were to form between an attached side chain molecule and a free side chain molecule the expected m/z would be 1160.4 m/z. The reaction solvent was then switched to DCM and L-alanine methyl ester hydrochloride was used as the side chain modification molecule. This reaction resulted in the formation of one new peak with a retention time of 18 min at roughly equal intensity to that of the MTM SA peak and a UV-Vis of 410 nm and a m/z of 1111.3. The calculated m/z of the expected molecule was 1111.4. The same conditions were used with L-valine methyl ester hydrochloride as well which resulted in a new molecule with a retention time of 20.6 min, a UV-Vis absorption of 410 nm and a m/z of 1139.5. The peak was the major product compared to the SA peak. The calculated m/z of the expected product was 1139.5. The reactions with L-glycine methyl ester hydrochloride and N,N-dimethylethylenediamine were then repeated with DCM as the solvent and PyBOP as the coupling agent. These reactions resulted in the formation of one new product with a retention time of 11.0 min for the N,N-dimethylethylenediamine reaction and 17.0 min for the L-glycine methyl ester hydrochloride reaction. Both products at a UV-Vis absorption of 410 nm and the m/z of the expected products identified previously. The individual peaks were collected from HPLC, the ACN removed, and freeze dried for use with the in vitro cytotoxicity assays.

Exemplary routes for synthesizing MTM SA and its use for 3-side chain derivatization are depicted in FIG. 2. Briefly, the mtmW deletion mutant of *Streptomyces argillaceus* M7W1 will be used, which produces ~50% MTM SA along with each 25% of MTMs SK and SDK. The unique carboxyl moiety of MTM SA allows a simple derivation into amides or esters. Initially short amide side chains will be generated using PyBop (benzotriazol-1-yl-oxytri-pyrrolidino-phosphonium hexafluoro-phosphate) or similar selective coupling reagents. The approach allows introducing N-atoms and other hydrogen bond donor and/or acceptor atoms into the side chain, thereby modifying its protein-binding properties. As an alternative to isolating MTM SA from the M7W1 mutant, the inventors also designed an enzymatic strategy using the premithramycin B (5) producing mtmOIV deletion mutant *S. argillaceus* M7O4 (production ~100 mg/L 5). FIG. 2 shows some examples of amino acid derivatives, including a set of MTM SA Trp derivatives some of which may be isotope-labeled variants to be used to mark hot-spots of interaction. As shown in FIG. 2, MTM SA can be isolated either from mutant M7W1 (20 mg/L) or enzymatically converted from premithramycin B, which is produced at 100 mg/L from the M7O4 mutant. Exemplary side chain modified molecules including MTM SA-Ala, -Ser, -Cys, -His, -Trp, -Tyr, -Phe, -PheGly, -Phe-Allylox are shown in FIG. 2.

Structure Confirmation by NMR

The structures of MTM SA-L-glycine methyl ester hydrochloride, MTM SA-L-alanine methyl ester hydrochloride, and MTM SA-L-valine methyl ester hydrochloride were confirmed by $H^1$ and $C^{13}$ NMR. The mass of the derivatives was also confirmed by mass spectrometry. For MTM SA-L-glycine methyl ester hydrochloride the expected mass+Na was 1120.45 and the observed mass was 1120.45, for MTM SA-L-alanine methyl ester hydrochloride the expected product had a calculated mass+Na of 1134.47 and the observed mass was 1134.47, and for MTM SA-L-valine methyl ester hydrochloride 1162.50 and observed mass was also 1162.50.

Example 2

In Vitro Cell Toxicity Assays

The cytotoxicity of a subgroup of the MTM SA analogues was tested against various Ewing sarcoma cell lines and non-Ewing sarcoma cell lines over a 72 hour period. Each analogue was checked individually with a range of concentrations to determine the $IC_{50}$ of the molecule in actively growing cell cultures. For comparison, the cytotoxicity of MTM and MTM SK, an analogue discovered previously and found to be more active than the regular MTM were also investigated. The $IC_{50}$ values are shown in Table 2 below.

TABLE 2

$IC_{50}$ values of MTM Analogs in Various Ewing Sarcoma and Non-Ewing Sarcoma Cell lines

| IC50 (nM) | EWING SARCOMA CELL LINES | | | | | | | | | | | | NON-EWING SARCOMA CELL LINES | | | | | | | |
|---|---|---|---|---|---|---|---|---|---|---|---|---|---|---|---|---|---|---|---|---|
| | TC 32 | 5838 | SK-ES-1 | A673 | TC71 | RDES | RH 30 | ES -2 | ES -3 | ES -4 | ES -7 | ES -8 | A549 | U118 | PC3 | DU 145 | C42 | VCaP | HCT-116 | OVCAR-8 |
| MTM | 28 | 43 | 26 | 36 | 25 | 36 | 47 | 42 | 51 | 22 | 32 | 37 | 63 | 48 | 57 | 31 | 81 | 33 | 29 | 26 |
| MTMSK | 23 | 23 | 25 | 37 | 31 | 40 | 62 | 39 | 56 | 32 | 42 | 44 | 30 | | 37 | 32 | 89 | 36 | 31 | 29 |
| MTMSA-Trp | 18 | 10 | 38 | 44 | 34 | 39 | 48 | 63 | 64 | 33 | 41 | 40 | 87 | 56 | 45 | 31 | 96 | 20 | 23 | 72 |
| MTMSA-Phe | | | | 109 | | 94 | 136 | 182 | 363 | 35 | 61 | 59 | 398 | | | | | 32 | 21 | |
| MTMSA-Tryptamine | 110 | 439 | 226 | | 78 | | | 155 | 216 | 90 | 86 | 97 | 196 | 76 | | | | | | |
| MTMSA-5-Br-Trp | 29 | 15 | 219 | | 68 | | | 159 | 210 | 102 | 76 | 50 | 316 | 59 | | | | | | |
| MTMSA-Me ester | 67 | 193 | 86 | | 46 | | | 76 | 90 | 41 | 51 | 47 | 99 | 38 | | | | | | |
| MTMSA-5-OMe Tryptamine | 73 | 78 | 63 | | 58 | | | 84 | 157 | 63 | 79 | 75 | 84 | 58 | | | | | | |
| MTMSA-Tyr | 133 | 170 | 306 | | 130 | | | 263 | 266 | 138 | 189 | 171 | 867 | 231 | | | | | | |
| MTMSA-Serotonin | 667 | 690 | 612 | | 671 | | | 749 | 658 | 610 | 753 | 676 | >3000 | 916 | | | | | | |
| MTM-Lys-2PGs | 6221 | | | | | | | | | | | | | | | | | | | |

Natural products are not always optimized for human purposes. Combining biosynthetic derivatization with chemical synthesis produces unique molecules unattainable by either method individually. Thus, a combination of these methods was used to modify the relatively inactive MTM SA that is accumulated alongside the biologically improved MTM analogues MTM SK and MTM SDK. The latter two molecules, which are both considerably more active and significantly less toxic than the natural product MTM itself, pointed in the direction that 3-side chain modifications can be advantageous. The modification of the 3-side chain of MTM SA with amino acid derivatives yielded several active compounds with the MTM SA-Trp and MTM SA-Phe, which exhibit high cytotoxicity against Ewing sarcoma cells and cancer cell specificity.

Example 3

Interaction Between MTM and the DNA Binding Domain of EWS-FLI1

A complex of MTM SA-Trp (a potent and highly selective analogue) with a strong binding double-stranded DNA oligomer (with the core sequence GGCC (SEQ ID NO:03)) was crystallized and the crystal structure of the complex was determined at 2.0 Å resolution. This crystal structure of the MTM-DNA complex provided a view of DNA recognition by MTM in atomic detail. The crystal structure of the complex showed that MTM SA-Trp is bound to DNA as a dimer, whose monomers are coordinated together by a divalent metal ion, consistent with previous NMR-molecular dynamics studies. Only five hydrogen bonds per MTM monomer are observed between MTM SA-Trp and DNA bases (direct and water-mediated), and they constitute a very minor fraction of the intermolecular contacts and do not appear to be sequence-specific. Indeed, MTM SA binds a variety of DNA sequences, as previously shown (Hampshire et al. (2008) *Biochimie* 90, 988-98). The majority of intermolecular contacts are made between the drug and the DNA backbone as MTM SA-Trp is bound to the minor groove of the DNA. Therefore, the DNA backbone conformation is likely a determining factor in MTM-DNA binding. Notably, the DNA in this structure is A-form, rather than B-form, providing a wide minor groove and a distinct relative base-pair disposition. To determine whether this DNA conformation is induced by MTM, the DNA was crystallized alone and its structure was determined at 1.65 Å resolution. The unbound DNA, similar to bound DNA, is A-form, suggesting that it is the A-form of the DNA and not the sequence alone (MTM is thought to bind GC-rich DNA) that is a determinant of MTM-DNA binding. Notably, the solvent-exposed 3-side chain of MTM SA-Trp bearing the Trp residue protrudes away from the DNA; it is positioned appropriately for interacting with DNA-binding factors.

Example 4

Binding of MTM/Analogues and EWS-FLI1/FLI1 DBD to DNA

MTM and its analogues are intrinsically fluorescent and their fluorescence decreases upon divalent metal-dependent dimerization. This property was used to establish (by titration of MgCl$_2$ into MTM/analogues) that at physiological salt concentration (5 mM MgCl2, 100 mM NaCl), MTM analogues are dimeric (not shown). The fluorescence of dimeric MTM is strongly (6-fold) enhanced upon DNA binding. By monitoring this fluorescence enhancement, the ability of MTM/analogues to bind several known A-form and B-form DNA oligomers was tested. In agreement with the crystal structure data, it was shown that MTM and its analogues display higher affinity for A-form DNA (e.g. Kd=2.7 µM for GGGATCCC (SEQ ID NO:04)), than for B-form DNA (e.g. Kd>15 µM for GGAATTCC (SEQ ID NO:05).

EWS-FLI1 and several constructs of FLI1 DNA binding domain (DBD) were expressed in *E. coli* and purified to homogeneity by a combination of Ni$^{2+}$-chelating and size exclusion chromatography. EWS-FLI1 required refolding, as described previously (Uren et al. (2004) *Biochemistry* 43, 13579-89), whereas FLI1 DBD were expressed as soluble proteins free from aggregation (not shown). An N-terminal deca-His tag (SEQ ID NO: 11) was cleaved by Prescission protease. These proteins displayed robust binding to consensus DNA containing the central GGAA (SEQ ID NO:06) recognition sequence and to a GGAA (SEQ ID NO:06) repeat sequence that is critical for EWS-FLI1 binding and oncogenesis in vivo (not shown).

Example 5

MTM SA Trp-FLI1 DBD-DNA Complex

The FLI1 DBD, which is the DNA interacting part of EWS-FLI1, is highly conserved in the ETS family of transcription factors, which include ERG, another protein found as a fusion with EWS in Ewing sarcomas. A recently reported crystal structure of ERG DBD in complex with the consensus DNA containing GGAA (SEQ ID NO:06) core (Regan et al. (2013) *Proceedings of the National Academy of Sciences of the United States of America* 110, 13374-9), shows that ERG DBD is bound in the major groove of the GGAA (SEQ ID NO:06) region, with the minor groove immediately upstream widened and A-form like. Because MTM binds to the minor groove of A-form DNA and ERG DBD, like FLI1 DBD, binds in the nearby major groove, binding of MTM and EWS-FLI1 to DNA is not competitive, but cooperative. Indeed, the model of MTM SA Trp positioned in (and stabilizing) the widened groove of the ERG DBD-DNA complex as observed in the crystal structure shows that the drug and the protein do not clash. The structural and biochemical data indicate that MTM and EWS-FLI1 bind to distinct neighboring structural regions of DNA via cooperative binding. Furthermore, the Trp side chain of MTM SA Trp and the terminal sugar moiety of the disaccharide tail of MTM interact with ERG DBD. This cooperative binding is responsible for the observed 1) highly potent (low-nM) antagonism of EWS-FLI1 by MTM and its analogues (FIG. 9), despite much weaker affinity (low-µM, at best) of MTM for DNA in the absence of other factors and 2) modulation of potency and anti-Ewing sarcoma selectivity in cell culture assays by modifications of the 3-side chain of MTM.

Example 6

Crystallization, Data Collection and Crystal Structure Determination of MTM SA Trp-DNA Complex 1 µL drops containing a mixture of 2 mM MTM SA Trp (diluted from a 20 mM DMSO stock) and 2 mM of 10-mer palindromic DNA (forms 1 mM of double-stranded DNA oligonucleotide by self-annealing in 10 mM sodium cacodylate, pH 6.5) having the sequence: 5'-AGAGGCCTCT-3' (SEQ ID NO:9) in 10 mM ZnCl$_2$ and 1 mM spermidine, were set up as hanging drops over 1 mL of the reservoir solutions of varying concentrations of MPD in the range 10-20% MPD. The crystals appeared within a week. The crystals were rapidly frozen in liquid nitrogen directly from the drop. The X-ray diffraction data were collected at the Advanced Photon Source, at Argonne National Laboratory. The crystal structure was determined by the single anomalous dispersion (SAD) method, by using the anomalous signal from $Zn^{2+}$. The crystal structure of MTM SA Trp-DNA complex was refined to the resolution of 2 Å. The crystals contain two complexes of mithramycin dimer with double-stranded DNA in the asymmetric unit.

Example 7

Modeling the Structure of the Ternary Complex of MTM SA Trp-DNA-ERG DNA Binding Domain An approximate model of a ternary complex of MTM SA-DNA-ERG DBD was constructed. The ERG DBD is nearly identical (with 98% sequence identity) to FLI1 DBD and MTM SA analogues are similarly active against EWS-ERG and EWS-FLI1 tumor cells. The atomic coordinates for all components of the model are given below. The side chain of the MTM SA molecule directly interacts with ERG. Specifically, the MTM interacting residues in ERG are: Tyr356, Lys363, His365, Gly366, Lys367, Arg368, Tyr369, Ala370.

FLI1 (SEQ ID NO: 07, FIG. 6) and ERG (SEQ ID NO:08, FIG. 7) contain nearly identical DNA binding domains and, therefore, all observations in this study that apply to the ERG DNA binding domain, apply to the FLI1 DNA binding domain. Accordingly, the MTM interacting residues of FLI1 are: Tyr343, Lys350, His352, Gly353, Lys354, Arg355, Tyr356, Ala357 of SEQ ID NO:07. For both ERG and FLI1, the MTM interacting residues are within the DNA binding domains of these proteins and correspond to residues Tyr68, Lys75, His77, Gly78, Lys79, Arg80, Tyr81, Ala82 of SEQ ID NO:01 & SEQ ID NO:02, provided in FIG. 8.

Example 8

Selectivity Assays-Ewing Sarcoma Cells Versus Non-Ewing Sarcoma Cells

Figure 9:
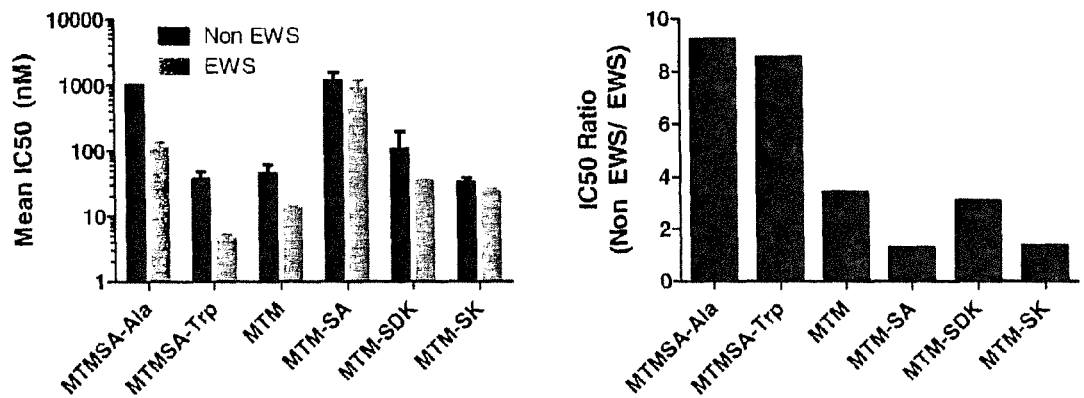
FIG. 9 illustrates the average absolute (left) and relative (right) cytotoxicity (to cell proliferation) of MTM and its analogues against Ewing sarcoma (EWS) relative to non-Ewing sarcoma cell lines.
Figure 10:
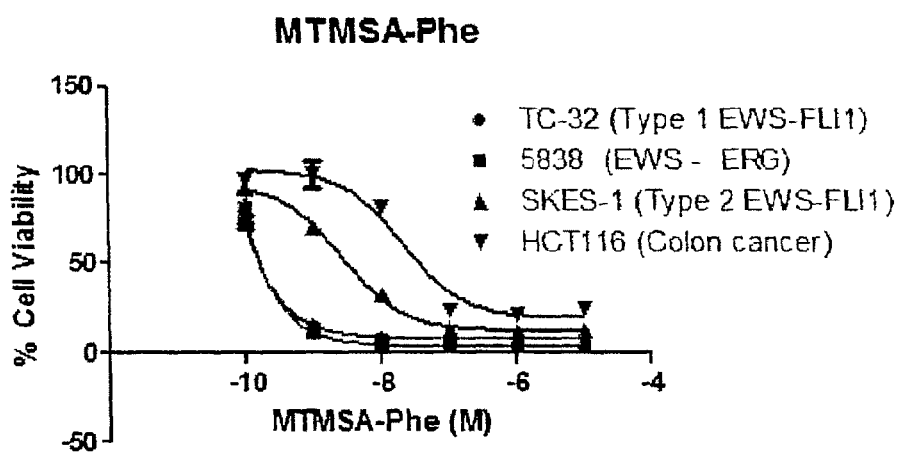
FIG. 10 shows the potency and specificity of MTM SA-Phe in killing of Ewing sarcoma cells.
Figure 11A:
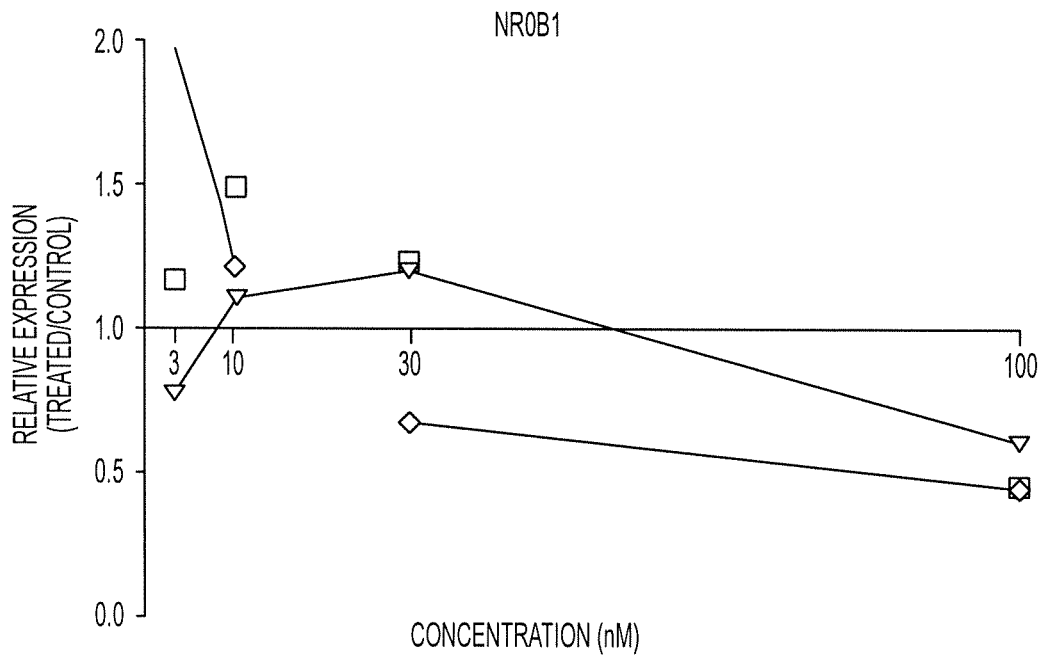
FIG. 11A, FIG. 11B, FIGS. 11C, 11D, and 11E provide a series of graphs showing that MTM analogs have increased cytoxicity and distinct cell cycle distribution in Ewing sarcoma. The graphs show relative gene expression in TC32 cells treated with MTM analogs. Three genes controlled by the EWS-FLI1 transcription factor were investigated by qRT-PCR at four different treatment concentrations for 6 hours. CCK served as a negative control.
Figure 11B:
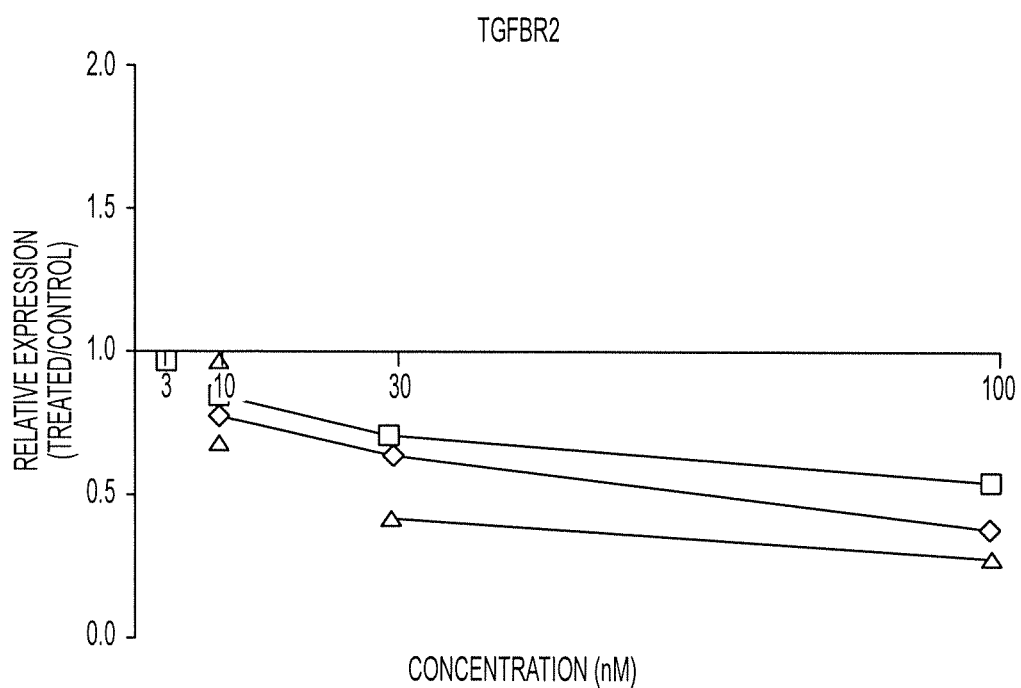
Figure 11C:
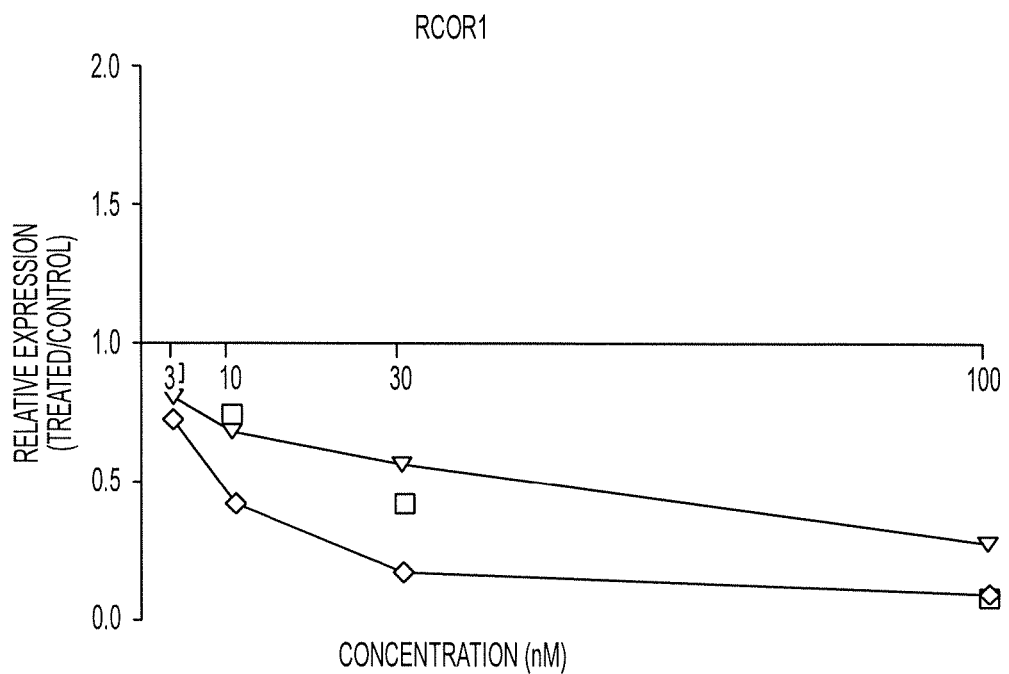
Figure 11D:
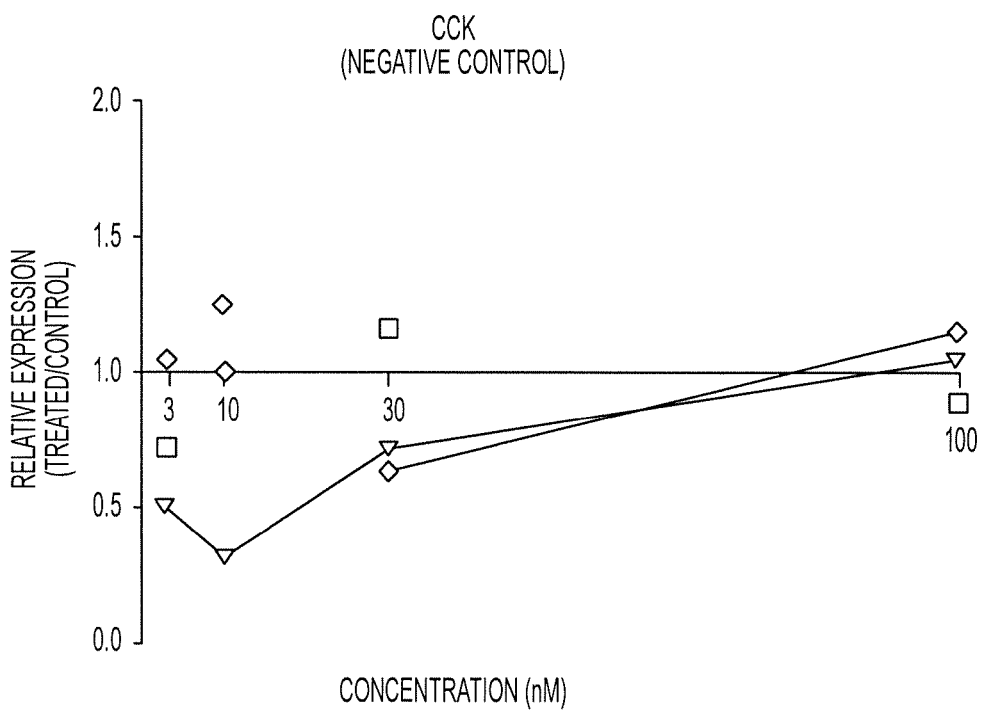
Figure 11E:
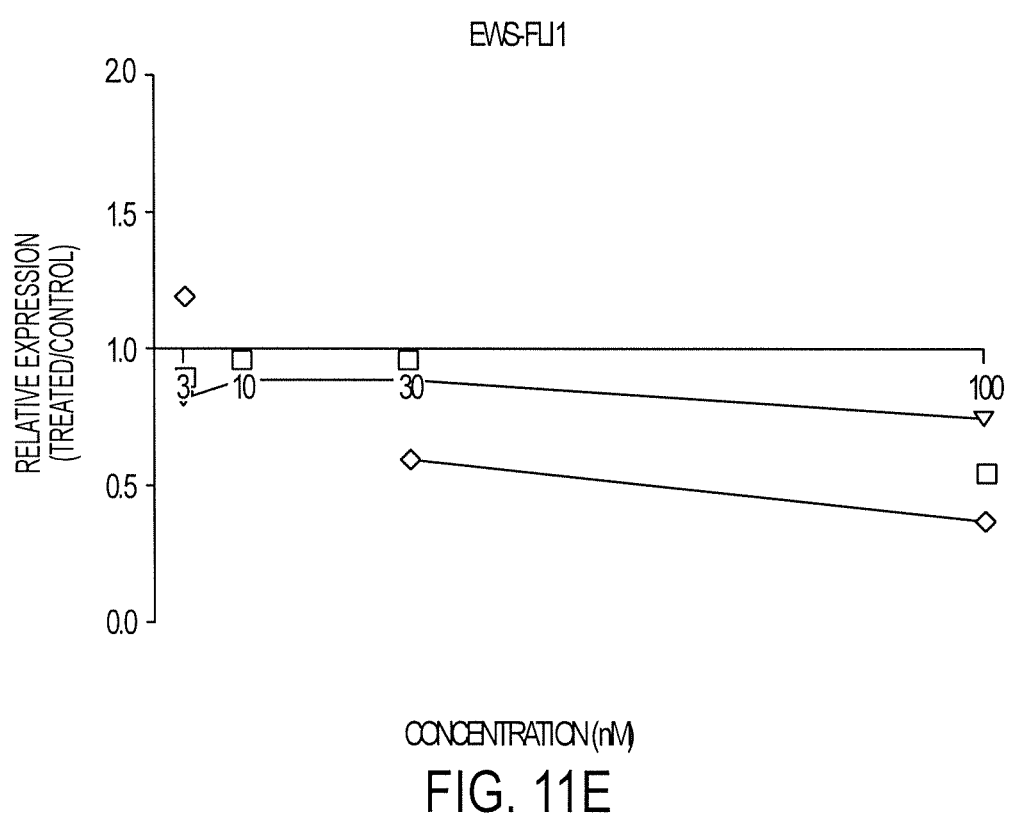

MTM analogues MTM SA-Ala and MTM SA-Trp display higher selectivity than MTM against Ewing sarcoma cells relative to non-Ewing cells (FIG. 9). Cytotoxicity of MTM and its analogues against a panel of actively growing Ewing sarcoma (TC32, 5838, SKES1) and non-Ewing (A459 (lung) and PC3 (prostate)) cancer cell lines were measured (72 hr). MTM displayed an $IC_{50}$=15 nM against the Ewing sarcoma panel. Remarkably, it was subsequently found that two MTM analogues, MTM SA-Ala and MTM SA-Trp show 3-fold higher selectivity than does MTM against Ewing sarcoma relative to non-Ewing cell lines (FIG. 9), with MTM SA-Ala being about 200-fold less potent than MTM, while MTM SA-Trp is about 3-fold more potent as well as 3-fold more selective than MTM against Ewing sarcoma cells. The modifications of the 3-side chain in MTM SA-Ala and MTM SA-Trp yielded 9-fold selectivity against Ewing sarcoma cells relative to non-Ewing cells (FIG. 9, right panel). MTM SA-Phe was surprisingly found to be even more potent and highly selective in killing of Ewing sarcoma cells than other MTM SA derivatives. As shown in FIG. 10, MTM SA-Phe showed significantly improved selectivity in the context of a target ETS transcription factor containing a DNA binding domain of SEQ ID NO:01 or SEQ ID NO:02.

Example 9

The Effect of MTM and its Analogues on EWS-FLI1-Mediated Transcription

Figure 12A:
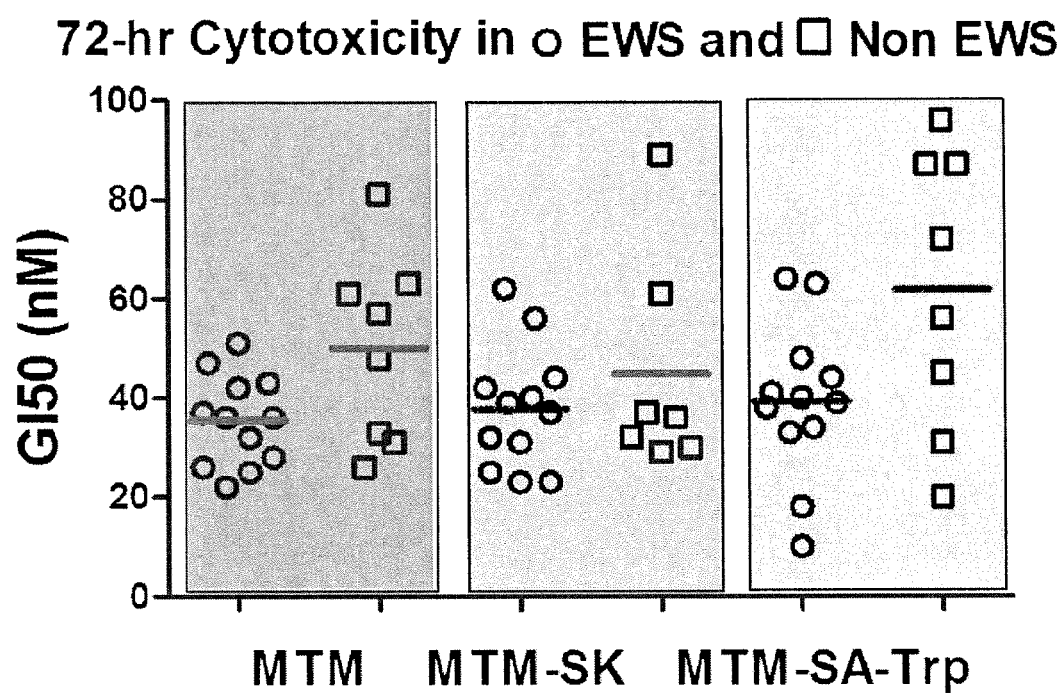
FIG. 12(a) shows the 72-hour cytotoxicity results in TC32, 5838, SK-ES-1, RD-ES, TC71, RH-30, A673, ES-2, ES-3, ES-4, ES-7, ES-8 Ewing sarcoma cell lines (o EWS) and A549, PC3, DU145, OVCAR-8, C42, VCap, LNCap, U118 non-Ewing sarcoma cell lines (☐Non-EWS).
Figure 12B:
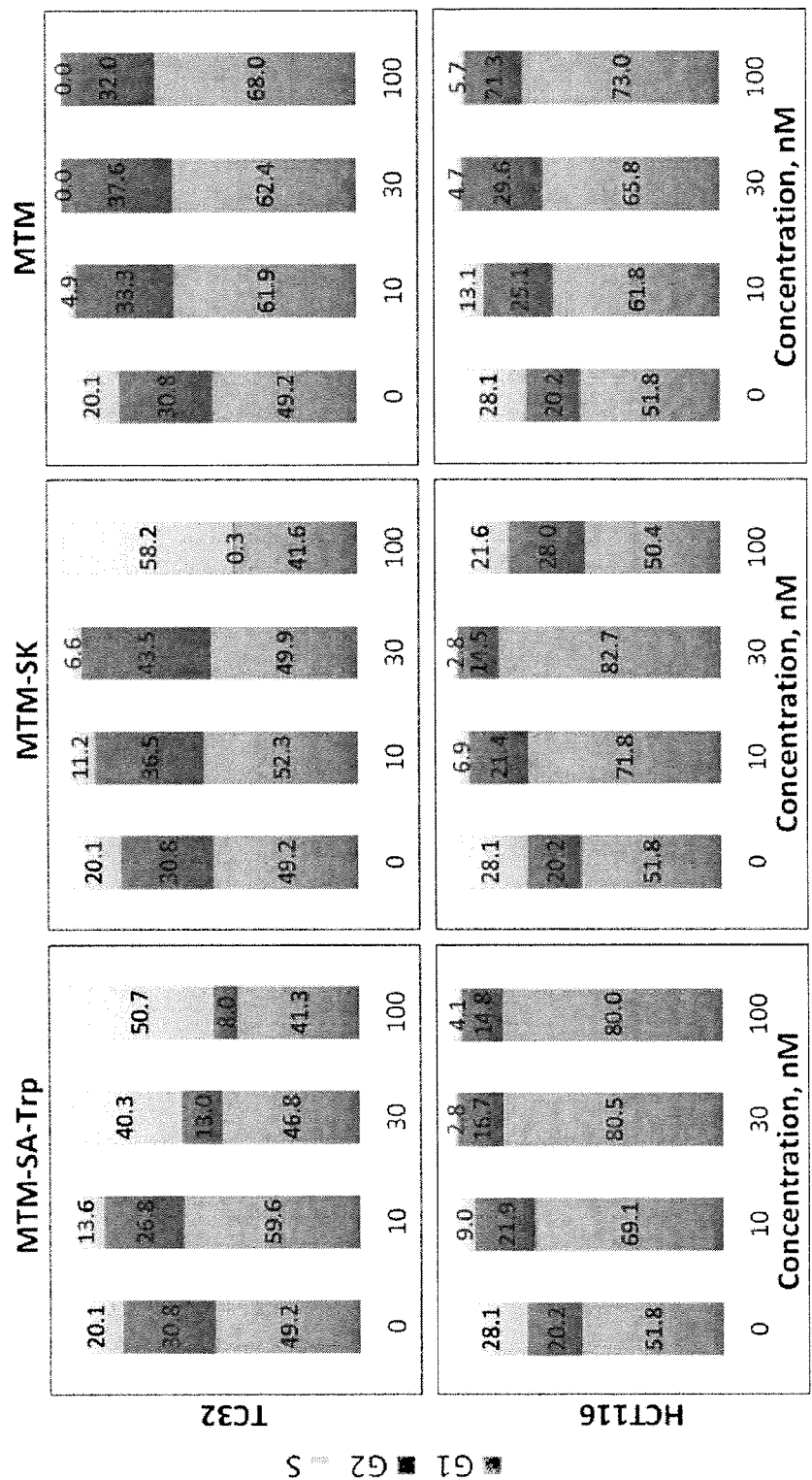
FIG. 12(b) is a FACs analysis of TC32 cells treated with 100 nM of drug for 24 hours.

Studies were conducted using MTM and lead analogs (mithramycin-SK (MTM-SK), mithramycin-SA-tryptophan (MTM-SA-Trp), and mithramycin-SA-phenylalanine (MTM-SA-Phe)). EWS-FLI1 promoter occupancy was investigated using chromatin immune precipitation real time PCR (ChIP-RTPCR). The effect of drug treatment on expression of genes controlled by EWSFLI1 was evaluated by quantitative real-time PCR (qRT-PCR) (FIG. 11). The effect of treatment with 100 nM of drug for 24 hours on cell cycle distribution was also compared among analogs (FIG. 12(b)). In vitro efficacy was evaluated by estimating $GI_{50}$ parameters (72-hr) (FIG. 12(a)). In addition, the maximum tolerated dose (MTD) and the effect of treatment on plasma total-calcium were used to assess relative toxicity in mice.

EWS-FLI1 promoter occupancy upstream from Nr0b1, Tgfbr2, and Rcor1 genes was evaluated in Ewing sarcoma cells (TC32 cells) by ChIP-RTPCR. MTM and MTM-SA-Trp analog destabilized FLI1 binding to all three promoters and MTM-SA-Trp was shown to be the most destabilizing. Comparatively, MTM-SK appears to mostly stabilize FLI1. Additionally, qRTPCR showed that MTM and its analogs efficiently down-regulated mRNA expression in a dose dependent manner (rank-order of efficiency: MTM-SA-Trp>MTM=MTM-SK). (FIG. 11). These data were in accord with the in vitro cytotoxicity data that show MTM-SA-Trp has relatively higher potency (lower $GI_{50}$) among Ewing cell lines (n=8) as compared to other analogs. (FIG. 12(a)). Furthermore, the effect of drug treatment appears to lead to differences in cell-cycle progression. MTM and MTM-SK treated TC32 cells were primarily in G1/G2 phase, whereas MTM-SA-Trp treated cells showed increased S-phase accumulation. (FIG. 12(b)).

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. An MTM SA derivative having the following formula:

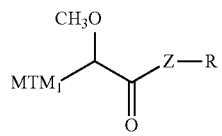

or a pharmaceutically acceptable salt thereof; wherein Z represents O, S, N—R'; R and R' represent, for each occurrence, H, alkyl, heterocyclic, aryl, heteroaryl, provided that R is not H when Z is O; ZR taken together represents an organic residue; and wherein $MTM_1$ represents the fused ring portion of the mithramycin structure and can include different sugars or sugar chains.

2. The MTM SA derivative according to claim 1 having the following formula:

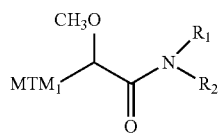

wherein $R_1$ and $R_2$ can be the same or different and each of $R_1$ and $R_2$ can be an H, an amino acid conjugate or an ester derivative thereof, a lower straight chain or branched alkyl unsubstituted or substituted with one or more amino, alkyl amino, alkylcarboxyl, alkoxyl, alkylcarbonyl, hydroxyl, thio, alkyldisulfide, halo, provided that $R_1$ and $R_2$ are not both H simultaneously.

3. The MTM SA derivative of claim 2, wherein $NR_1R_2$ form a phenylalanine (Phe) conjugate or an ester derivative thereof.

4. The MTM SA derivative of claim 2, wherein $NR_1R_2$ form a tryptophan (Trp) conjugate or an ester derivative thereof.

5. The MTM SA derivative of claim 3 wherein the phenylalanine is substituted with an indole alkyl group.

6. The MTM SA derivative of claim 4 wherein the tryptophan is substituted with a phenyl alkyl group.

7. A method of preparing the MTM SA derivative of claim 2, the method comprising coupling the terminal carboxylic acid group of MTM SA with an amine.

8. A method of treating cancer or neuro-disease in a patient in need thereof, the method comprising administering to the patient a therapeutically effective amount of the MTM SA derivative or a pharmaceutically acceptable salt thereof of claim 1.

9. The method of claim 8, wherein the method comprises treating Ewing sarcoma.

10. The method of claim 8, wherein the method comprises treating lung cancer.

11. The method of claim 8, wherein the method comprises treating colon cancer.

12. The method of claim 9 wherein the MTM SA derivative is a substituted or unsubstituted MTM SA-Trp or an ester derivative thereof or a pharmaceutically acceptable salt thereof.

13. The method of claim 9 wherein the MTM SA derivative is a substituted or unsubstituted MTM SA-Phe or an ester derivative thereof or a pharmaceutically acceptable salt thereof.

14. A method for selectively modulating the activity of a target ETS transcription factor in a patient in need thereof, including administering to the patient a therapeutically effective amount of an MTM SA derivative or a pharmaceutically acceptable salt thereof of claim 2.

15. The method of claim 14, wherein the MTM SA derivative is a substituted or unsubstituted MTM SA-Phe or an ester derivative thereof or a pharmaceutically acceptable salt thereof.

16. The method of claim 14, wherein the MTM SA derivative is a substituted or unsubstituted MTM SA-Trp or an ester derivative thereof or a pharmaceutically acceptable salt thereof.

* * * * *

SEQUENCE LISTING

<160> NUMBER OF SEQ ID NOS: 11

<210> SEQ ID NO 1
<211> LENGTH: 98
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 1
```

Pro Gly Ser Gly Gln Ile Gln Leu Trp Gln Phe Leu Leu Glu Leu Leu
1               5                   10                  15

Ser Asp Ser Ala Asn Ala Ser Cys Ile Thr Trp Glu Gly Thr Asn Gly
            20                  25                  30

Glu Phe Lys Met Thr Asp Pro Asp Glu Val Ala Arg Arg Trp Gly Glu
        35                  40                  45

Arg Lys Ser Lys Pro Asn Met Asn Tyr Asp Lys Leu Ser Arg Ala Leu
    50                  55                  60

Arg Tyr Tyr Tyr Asp Lys Asn Ile Met Thr Lys Val His Gly Lys Arg
65                  70                  75                  80

Tyr Ala Tyr Lys Phe Asp Phe His Gly Ile Ala Gln Ala Leu Gln Pro
                85                  90                  95

His Pro

```
<210> SEQ ID NO 2
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

Pro Gly Ser Gly Gln Ile Gln Leu Trp Gln Phe Leu Leu Glu Leu Leu
1               5                   10                  15

Ser Asp Ser Ser Asn Ser Ser Cys Ile Thr Trp Glu Gly Thr Asn Gly
            20                  25                  30

Glu Phe Lys Met Thr Asp Pro Asp Glu Val Ala Arg Arg Trp Gly Glu
        35                  40                  45

Arg Lys Ser Lys Pro Asn Met Asn Tyr Asp Lys Leu Ser Arg Ala Leu
    50                  55                  60

Arg Tyr Tyr Tyr Asp Lys Asn Ile Met Thr Lys Val His Gly Lys Arg
65                  70                  75                  80

Tyr Ala Tyr Lys Phe Asp Phe His Gly Ile Ala Gln Ala Leu Gln Pro
                85                  90                  95

His Pro

```
<210> SEQ ID NO 3
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 ggcc                                                                   4

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 4 gggatccc                                                                          8

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 ggaattcc                                                                          8

<210> SEQ ID NO 6
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ggaa                                                                              4

<210> SEQ ID NO 7
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Gly Thr Ile Lys Glu Ala Leu Ser Val Val Ser Asp Asp Gln
1               5                   10                  15

Ser Leu Phe Asp Ser Ala Tyr Gly Ala Ala His Leu Pro Lys Ala
            20                  25                  30

Asp Met Thr Ala Ser Gly Ser Pro Asp Tyr Gly Gln Pro His Lys Ile
        35                  40                  45

Asn Pro Leu Pro Pro Gln Gln Glu Trp Ile Asn Gln Pro Val Tyr Val
    50                  55                  60

Asn Val Lys Arg Glu Tyr Asp His Met Asn Gly Ser Arg Glu Ser Pro
65                  70                  75                  80

Val Asp Cys Ser Val Ser Lys Cys Ser Lys Leu Val Gly Gly Gly Glu
                85                  90                  95

Ser Asn Pro Met Asn Tyr Asn Ser Tyr Met Asp Glu Lys Asn Gly Pro
            100                 105                 110

Pro Pro Pro Asn Met Thr Thr Asn Glu Arg Arg Val Ile Val Pro Ala
        115                 120                 125

Asp Pro Thr Leu Trp Thr Gln Glu His Val Arg Gln Trp Leu Glu Trp
    130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr

```
            195                 200                 205
Asp Gln Ser Ser Arg Leu Ser Val Lys Glu Asp Pro Ser Tyr Asp Ser
    210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
        275                 280                 285

Glu Leu Leu Ser Asp Ser Ala Asn Ala Ser Cys Ile Thr Trp Glu Gly
    290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
        355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
        435                 440                 445

Gly Ser Tyr Tyr
    450

<210> SEQ ID NO 8
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95
```

```
Gly Gly Lys Met Val Gly Ser Pro Asp Thr Val Gly Met Asn Tyr Gly
                100                 105                 110
Ser Tyr Met Glu Glu Lys His Met Pro Pro Asn Met Thr Thr Asn
        115                 120                 125
Glu Arg Arg Val Ile Val Pro Ala Asp Pro Thr Leu Trp Ser Thr Asp
    130                 135                 140
His Val Arg Gln Trp Leu Glu Trp Ala Val Lys Glu Tyr Gly Leu Pro
145                 150                 155                 160
Asp Val Asn Ile Leu Leu Phe Gly Asn Ile Asp Gly Lys Glu Leu Cys
                165                 170                 175
Lys Met Thr Lys Asp Asp Phe Gln Arg Leu Thr Pro Ser Tyr Asn Ala
            180                 185                 190
Asp Ile Leu Leu Ser His Leu His Tyr Leu Arg Glu Thr Pro Leu Pro
            195                 200                 205
His Leu Thr Ser Asp Asp Val Asp Lys Ala Leu Gln Asn Ser Pro Arg
    210                 215                 220
Leu Met His Ala Arg Asn Thr Asp Leu Pro Tyr Glu Pro Pro Arg Arg
225                 230                 235                 240
Ser Ala Trp Thr Gly His Gly His Pro Thr Pro Gln Ser Lys Ala Ala
                245                 250                 255
Gln Pro Ser Pro Ser Thr Val Pro Lys Thr Glu Asp Gln Arg Pro Gln
            260                 265                 270
Leu Asp Pro Tyr Gln Ile Leu Gly Pro Thr Ser Ser Arg Leu Ala Asn
            275                 280                 285
Pro Gly Ser Gly Gln Ile Gln Leu Trp Gln Phe Leu Leu Glu Leu Leu
    290                 295                 300
Ser Asp Ser Ser Asn Ser Ser Cys Ile Thr Trp Glu Gly Thr Asn Gly
305                 310                 315                 320
Glu Phe Lys Met Thr Asp Pro Asp Glu Val Ala Arg Arg Trp Gly Glu
                325                 330                 335
Arg Lys Ser Lys Pro Asn Met Asn Tyr Asp Lys Leu Ser Arg Ala Leu
            340                 345                 350
Arg Tyr Tyr Tyr Asp Lys Asn Ile Met Thr Lys Val His Gly Lys Arg
            355                 360                 365
Tyr Ala Tyr Lys Phe Asp Phe His Gly Ile Ala Gln Ala Leu Gln Pro
370                 375                 380
His Pro Pro Glu Ser Ser Leu Tyr Lys Tyr Pro Ser Asp Leu Pro Tyr
385                 390                 395                 400
Met Gly Ser Tyr His Ala His Pro Gln Lys Met Asn Phe Val Ala Pro
                405                 410                 415
His Pro Pro Ala Leu Pro Val Thr Ser Ser Ser Phe Phe Ala Ala Pro
            420                 425                 430
Asn Pro Tyr Trp Asn Ser Pro Thr Gly Gly Ile Tyr Pro Asn Thr Arg
            435                 440                 445
Leu Pro Thr Ser His Met Pro Ser His Leu Gly Thr Tyr Tyr
    450                 455                 460

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```

```
agaggcctct                                                        10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 11

His His His His His His His His His His
1               5                   10
```